(12) United States Patent
Cohen et al.

(10) Patent No.: US 11,001,005 B2
(45) Date of Patent: May 11, 2021

(54) ASEPTIC PRINTER SYSTEM INCLUDING DUAL-ARM MECHANISM

(71) Applicant: TDBT IP Inc., New York, NY (US)

(72) Inventors: Daniel L. Cohen, Brooklyn, NY (US);
Scott D. Cornez, New York, NY (US);
Jerson Mezquita, Bronx, NY (US)

(73) Assignee: TDBT IP INC., New York, NY (US)

( * ) Notice: Subject to any disclaimer, the term of this patent is extended or adjusted under 35 U.S.C. 154(b) by 235 days.

(21) Appl. No.: 15/988,922

(22) Filed: May 24, 2018

(65) Prior Publication Data

US 2018/0339455 A1     Nov. 29, 2018

Related U.S. Application Data

(60) Provisional application No. 62/511,292, filed on May 25, 2017.

(51) Int. Cl.
| | |
|---|---|
| *B29C 64/364* | (2017.01) |
| *B29C 64/25* | (2017.01) |
| *C12M 3/00* | (2006.01) |
| *C12M 1/26* | (2006.01) |
| *B29C 64/307* | (2017.01) |

(Continued)

(52) U.S. Cl.
CPC ........... *B29C 64/364* (2017.08); *B25J 18/002* (2013.01); *B29C 64/106* (2017.08); *B29C 64/209* (2017.08); *B29C 64/245* (2017.08); *B29C 64/25* (2017.08); *B29C 64/307* (2017.08); *B33Y 10/00* (2014.12); *B33Y 30/00* (2014.12); *B33Y 40/00* (2014.12); *C12M 21/08* (2013.01);

(Continued)

(58) Field of Classification Search
CPC ....... B29C 64/364; B33Y 10/00; B33Y 30/00; B33C 64/245
See application file for complete search history.

(56) References Cited

U.S. PATENT DOCUMENTS

| | | |
|---|---|---|
| 5,121,329 A | 6/1992 | Crump |
| 5,126,529 A | 6/1992 | Weiss et al. |

(Continued)

FOREIGN PATENT DOCUMENTS

| | | |
|---|---|---|
| WO | WO-2005/057436 A1 | 6/2005 |
| WO | WO-2017/040975 A1 | 3/2017 |

OTHER PUBLICATIONS

U.S. Appl. No. 16/023,153, filed Jun. 29, 2018, Lipson et al.

(Continued)

*Primary Examiner* — Nathan T Leong
(74) *Attorney, Agent, or Firm* — Foley & Lardner LLP; Sunit Talapatra

(57) ABSTRACT

A system and method are provided for fabricating 3D structures from biomaterial. The system includes a printer assembly having a dual-arm assembly including an upper arm, and a lower arm connected by an elbow joint to the upper arm. A disposable barrier encloses a printing surface from an external environment and from components of the printer assembly. The upper arm and lower arm are inserted into an inlet of the barrier, so as to be isolated from the print surface. The lower arm is provided with an extruding system, and the extruding system includes an actuator-driven syringe configured to deposit biomaterial on the print surface. The biomaterial is deposited on the print surface to carry out 3D fabrication in an aseptic environment.

14 Claims, 12 Drawing Sheets

(51) Int. Cl.
  *B25J 18/00* (2006.01)
  *B33Y 10/00* (2015.01)
  *B33Y 30/00* (2015.01)
  *B33Y 40/00* (2020.01)
  *B29C 64/245* (2017.01)
  *B29C 64/209* (2017.01)
  *B29C 64/106* (2017.01)
  *B33Y 70/00* (2020.01)
  *B29K 105/00* (2006.01)

(52) U.S. Cl.
  CPC ..... *C12M 33/00* (2013.01); *B29K 2105/0061* (2013.01); *B33Y 70/00* (2014.12)

(56) References Cited

U.S. PATENT DOCUMENTS

| | | |
|---|---|---|
| 5,134,569 A | 7/1992 | Masters |
| 5,204,055 A | 4/1993 | Sachs et al. |
| 5,260,009 A | 11/1993 | Penn |
| 5,312,224 A | 5/1994 | Batchelder et al. |
| 5,518,680 A | 5/1996 | Cima et al. |
| 5,900,207 A | 5/1999 | Danforth et al. |
| 6,030,199 A * | 2/2000 | Tseng ............ B29C 41/12 425/132 |
| 6,036,777 A | 3/2000 | Sachs |
| 6,153,034 A | 11/2000 | Lipsker |
| 6,224,893 B1 | 5/2001 | Langer et al. |
| 6,251,340 B1 | 6/2001 | Tseng |
| 6,658,314 B1 | 12/2003 | Gothait |
| 6,773,713 B2 | 8/2004 | Bonassar et al. |
| 6,850,334 B1 | 2/2005 | Gothait |
| 6,905,738 B2 | 6/2005 | Ringeisen et al. |
| 6,986,739 B1 | 1/2006 | Warren et al. |
| 7,168,935 B1 | 1/2007 | Taminger et al. |
| 7,195,475 B2 | 3/2007 | Silverbrook |
| 7,220,112 B2 | 5/2007 | Silverbrook |
| 7,220,115 B2 | 5/2007 | Silverbrook |
| 7,306,323 B2 | 12/2007 | Silverbrook |
| 7,322,674 B2 | 1/2008 | Silverbrook |
| 7,625,198 B2 | 12/2009 | Lipson et al. |
| 7,939,003 B2 | 5/2011 | Bonassar et al. |
| 8,636,938 B2 | 1/2014 | Bonassar et al. |
| 8,877,112 B2 | 11/2014 | Bonassar et al. |
| 9,242,031 B2 | 1/2016 | Bonassar et al. |
| 10,034,964 B2 | 7/2018 | Bonassar et al. |
| 2002/0149137 A1 | 10/2002 | Jang et al. |
| 2002/0159982 A1 | 10/2002 | Bonassar et al. |
| 2002/0182241 A1 | 12/2002 | Borenstein et al. |
| 2003/0170285 A1 | 9/2003 | Veazey et al. |
| 2004/0094058 A1 | 5/2004 | Kasperchik et al. |
| 2004/0143358 A1 | 7/2004 | Silverbrook |
| 2004/0237822 A1 | 12/2004 | Boland et al. |
| 2005/0253308 A1 | 11/2005 | Sherwood |
| 2006/0156978 A1 | 7/2006 | Lipson et al. |
| 2006/0160250 A1 | 7/2006 | Bonassar et al. |
| 2007/0182799 A1 | 8/2007 | Silverbrook |
| 2008/0001997 A1 | 1/2008 | Silverbrook |
| 2008/0062214 A1 | 3/2008 | Silverbrook |
| 2008/0068416 A1 | 3/2008 | Silverbrook |
| 2008/0084450 A1 | 4/2008 | Silverbrook |
| 2012/0193335 A1 | 8/2012 | Guldberg |
| 2013/0001829 A1* | 1/2013 | Halter ............ B29C 45/5008 264/328.1 |
| 2013/0089642 A1* | 4/2013 | Lipson ............ B29C 64/209 426/115 |
| 2013/0209600 A1 | 8/2013 | Tow |
| 2014/0050811 A1 | 2/2014 | Lipton et al. |
| 2015/0035206 A1 | 2/2015 | Maggiore |
| 2015/0105891 A1 | 4/2015 | Golway et al. |
| 2016/0240406 A1* | 8/2016 | Kajihara ............ F25B 9/14 |
| 2016/0297152 A1 | 10/2016 | Maggiore |

OTHER PUBLICATIONS

Chang et al., "Injection Molding of Chondrocyte/Alginate Constructs in the Shape of Facial Implants," J. Biomed. Mat. Res. 55:503-511 (2001).

Cohen et al., "Direct Freeform Fabrication of Spatially Heterogeneous Living Pre-Cell-Seeded Implants," Proceedings of the 15th Solid Freeform Fabrication Symposium, Austin TX(2004).

Czaplewski et al., "Nanofluidic Channels with Elliptical Cross Sections Formed Using a Nonlithographic Process," Applied Physics Letters 83(23): 4836-4838 (2003).

Czaplewski et al., "Nonlithographic Approach to Nanostructure Fabrication Using a Scanned Electrospinning Source," J.Vac. Sci. Technol. B 21(6):2994-2997 (2003).

Fuller et al., "Ink-jet Printed Nanoparticle Microelectromechanical Systems," Journal of Microelectromechanical Systems 11:54-60 (2002).

Gene et al., "Effect of Substrate Mechanics on Chondrocyte Adhesion to Modified Alginate Surfaces," Arch. Biochem. Biophys. 422:161-167 (2004).

Hung et al., "Anatomically Shaped Osteochondral Constructs for Articular Cartilage Repair", J. Biomech. 36:1853-1864 (2003).

Kameoka et al., "Fabrication of Oriented Polymeric Nanofibers on Planar Surfaces by Electrospinning," Applied Physics Letters 83(2):371-373 (2003).

Kameoka et al., "A Scanning Tip Electrospinning Source for Deposition of Oriented Nanofibres," Nanotechnology 14:1124-1129 (2003).

Kameoka et al., "Fabrication of Suspended Silica Glass Nanofibers from Polymeric Materials Using a Scanned Electrospinning Source," Nano Letters 4(11):2105-2108 (2004).

Kameoka et al., "Polymeric Nanowire Architecture," J. Mater. Chem. 14:1503-1505 (2004).

Kim et al., "Experimental Model for Cartilage Tissue Engineering to Regenerate the Zonal Organization of Articular Cartilage," Osteoarthritis Cartilage 00:1-12 (2003).

Klein et al., "Tissue Engineering of Stratified Articular Cartilage from Chondrocyte Subpopulations," Osteoarthritis Cartilage 11:595-602 (2003).

Landers et al., "Desktop Manufacturing of Complex Objects, Prototypes and Biomedical Scaffolds by Means of Computer-Assisted Design Combined with Computer-guided 3D Plotting of Polymers and Reactive Oligomers," Macromol. Mater.Eng. 282:17-21 (2000).

Lipson & Bongard, "An Exploration-Estimation Algorithm for Synthesis and Analysis of Engineering Systems Using Minimal Physical Testing," Proceedings of the ASME Design Automation Conference (DAC04), Salt Lake City, UT (2004).

Malone & Lipson, "Freeform Fabrication of Electroactive Polymer Actuators and Electromechanical Devices," Proceedings of the 15th Solid Freeform Fabrication Symposium, Austin, TX (2004).

Malone & Lipson, "Functional Freeform Fabrication for Physical Artificial Life," Proceedings of the 9th International Conference on Artificial Life (ALIFE IX) (2004).

Malone & Lipson, "Solid Free-Form Fabrication for Self-Sustained Robot Ecologies: Challenges and Opportunities," Proceedings of Robosphere 2002, NASA Ames Research Center, CA, USA (2002).

Malone & Lipson, "Solid Freeform for Autonomous Manufacturing of Complete Mobile Robots," Proceedings of Robosphere 2004, NASA Ames Research Center, CA, USA (2004).

Malone & Purwin, "Application of Machine Learning Methods to the Open-Loop Control of a Freeform Fabrication System," Proceedings of the 15th Solid Freeform Fabrication Symposium, Austin, TX (2004).

Malone et al., "Freeform Fabrication of Zinc-Air Batteries and Electromechanical Assemblies," Proceedings of the 14th Solid Freeform Fabrication Symposium, Austin, TX (2003).

Malone et al., "Freeform Fabrication of Zinc-Air Batteries and Electromechanical Assemblies," Rapid Prototyping Journal 10(1): 58-69 (2004).

Mironov et al., "Organ Printing: Computer-Aided Jet-based 3D Tissue Engineering," Trends in Biotechnology 21 (4): 157-161 (2003).

(56) References Cited

OTHER PUBLICATIONS

Ouyang et al., "Rapid Prototyping and Characterization of a WC-(NiSiB Alloy) Ceramet/Tool Steel Functionally Graded Material (FGM) Synthesized by Laser Cladding," in Rapid Prototyping of Materials, F.D.S Marquis and D.L. Bourell Eds., TMS (The Minerals, Metals & Materials Society) 77-93 (2002).
Pfister et al., "Biofunctional Rapid Prototyping for Tissue-Engineering Applications: 3D Bioplotting Versus 3D Printing," Journal of Polymer Science Part A: Polymer Chemistry 42:624-638 (2004).
Roth et al., "Inkjet Printing for High-Throughput Cell Patterning," Biomaterials 25:3707-3715 (2004).
Smurov et al., "Laser-assisted Direct Manufacturing of Functionally Graded 3D Objects by Coaxial Powder Injection," Proceedings of the SPIE—The International Society for Optical Engineering 5399:27-37 (2004).
Sun et al., "Multi-nozzle Biopolymer Deposition for Tissue Engineering Application," 6th International Conference on Tissue Engineering, Orlando, FL (Oct. 10-13, 2003)(Abstract only).
Xu et al., "Injectable Tissue-Engineered Cartilage with Different Chondrocyte Sources," Plast. Reconstr. Surg. 113(5):1361-1371 (2004).
Grunert et al., "Annular repair using high-density collagen. An in vivo study", European Cells and Materials, vol. 26, suppl. 8, 2013, p. 15.
Ibusuki et al., "Photochemically Cross-Linked Collagen Gels as Three-Dimensional Scaffolds for Tissue Engineering", Tissue Engineering, vol. 13, No. 8, 2007.
Sher, Davide, "The top 15 bioprinters", Aug. 26, 2015, 3D Printer Industry, accessed at Internet URL:https://3dprintingindustry.com/news/top-10-bioprinters-55699/.

\* cited by examiner

ASEPTIC PRINTER SYSTEM INCLUDING DUAL-ARM MECHANISM

CROSS-REFERENCE TO RELATED APPLICATIONS

The present application claims the benefit of priority to U.S. Provisional Patent Application Ser. No. 62/511,292, filed on May 25, 2017, the entire contents of which are hereby incorporated by reference.

BACKGROUND

The present technology relates generally to printing systems for printing biomaterial and methods of printing via such systems. More particularly, the present technology relates to systems and methods for printing biomaterial, such as collagen-containing 3D printing bio gels, to fabricate 3D structures of biomaterial.

Many 3D printing technology applications involve printing of various inorganic or organic substances which are not used, for example, in tissue engineering. In tissue engineering implementations, it is important for fabricated structures to be made in an aseptic manner. Existing 3D manufacturing systems, e.g., additive manufacturing systems, have exposed parts that cannot be effectively aseptically cleaned. Further, existing print systems have morphologies that not only impede efficient aseptic cleaning, but constrain printer performance due to mechanical assemblies which require lengthy set-up times and have complicated movements over printed constructs.

The present technology is directed to overcoming these and other deficiencies.

SUMMARY

In at least one embodiment, a printer system comprises an arm assembly connected to a printer housing; a print surface above which a deposition tip connected to the arm assembly is configured to deposit material; and a barrier surrounding the print surface, the barrier being structured to isolate the print surface from the arm assembly. Moreover, in at least one embodiment, a level of assured sterility is reliably achieved. Additionally, the printer system includes one or more components which may be readily washed down, further mitigating the risk of cross contamination.

In another embodiment, a method of using a printing system comprising a printer assembly to fabricate one or more structures comprises attaching a disposable barrier to the printer assembly; preparing biomaterial to be deposited on a print surface; supplying the biomaterial to a deposition tip coupled to the printer assembly; and depositing, by the deposition tip, the biomaterial on the print surface, wherein the print surface is enclosed within the disposable barrier.

In yet another embodiment, a printer system comprises an arm assembly including a first arm configured to be driven by a first motor, a second arm configured to be driven by a second motor, and an extruding system including a deposition tip configured to deposit material on a print surface; a lead screw which at least one of the first motor or the second motor is configured to rotate via a coupler; and a lead screw nut configured to travel along the lead screw so as to rotate a linkage communicated with the first arm, wherein at least the first motor, the second motor, the lead screw and the lead screw nut are encased so as to be isolated from an outside environment.

In at least one further embodiment, a method of assembling an aseptic printer includes attaching a receptacle to a valve configured to control ingress of material to the receptacle; attaching a deposition tip to the receptacle; securing, in a holder, the receptacle assembled with the valve and deposition tip; and disposing the holder and a print platform in a disposable barrier.

BRIEF DESCRIPTION OF THE DRAWINGS

The details of one or more embodiments are set forth in the accompanying drawings and the description below. Other features, aspects, and advantages of the disclosure will become apparent from the description, the drawings, and the claims. In the drawings, like reference numerals are used throughout the various views to designate like components.

Figure 1A:
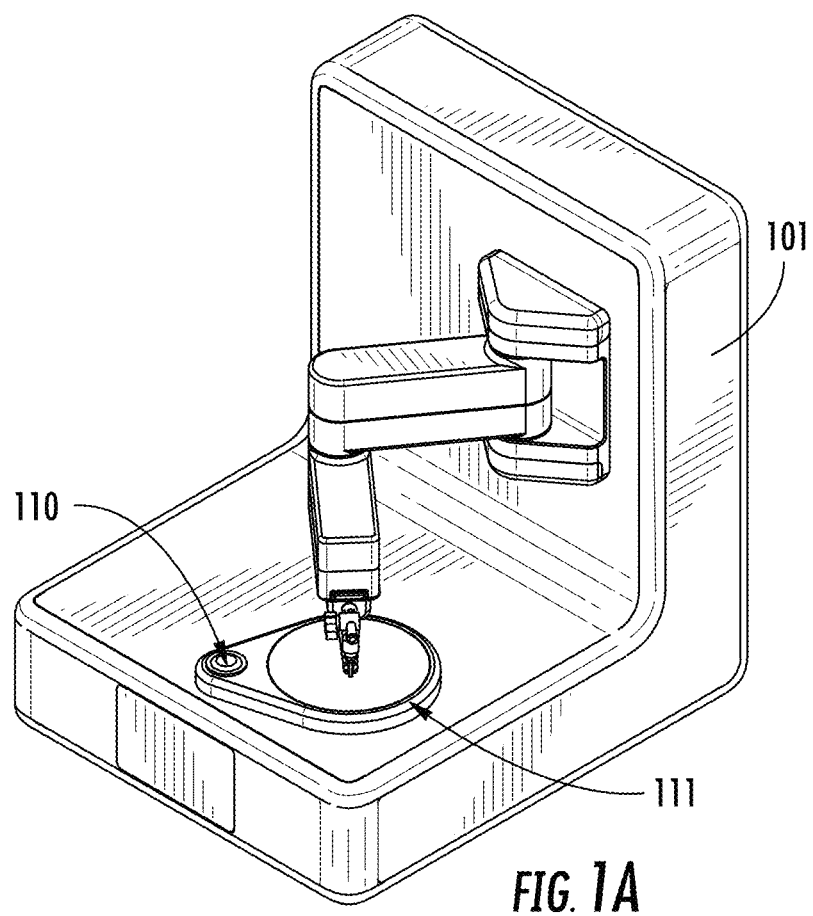
FIG. 1A is a perspective view of a system according to an embodiment.

It will be recognized that some or all of the figures are schematic representations for purposes of illustration. The figures are provided for the purpose of illustrating one or more embodiments with the explicit understanding that they will not be used to limit the scope or the meaning of the claims.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout and are as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of refereeing individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified. The expression "comprising" means "including, but not limited to."

Thus, other non-mentioned substances, additives, carriers, or steps may be present. Unless otherwise specified, "a" or "an" means one or more.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Any numerical parameter should at least be construed in light of the number reported significant digits and by applying ordinary rounding techniques. The term "about" when used before a numerical designation, e.g., temperature, time, amount, and concentration including range, indicates approximations which may vary by (+) or (−) 10%, 5% or 1%.

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

In some embodiments, the term "gel" includes, but is not limited to, non-Newtonian fluids and Bingham plastics.

As used herein, the term "viscosity" refers to the resistance to gradual deformation by shear stress or tensile stress of a material.

As used herein, the term "shear stress" or "shear-thinning" refers to the rheological viscoelastic properties of a material related to fluid-like or non-fluid-like behavior and flow. Shear stress and shear-thinning include properties related to Bingham flow, plastic flow, pseudoplasticity, dilatancy, thixotropy, rheopexy, and the like or other stress and/or strain properties of a viscous material. Further, "shear-thinning" refers to a reduction in apparent viscosity (the ratio of shear stress to the shear rate) with increasing (pseudoplastic), time dependent (thixotropic) or associated with a yield stress, defined as a stress that must be exceeded before flow starts, (Bingham plastics and generalized Bingham plastics). See, generally, Harris, J., & Wilkinson, W. L., "Non-Newtonian Fluid," pp. 856-858 in Parker, S. P., ed., McGraw-Hill Encyclopedia of Physics, Second Edition, McGraw-Hill, New York, 1993. A suitable viscosity range of the present technology includes, but is not limited to, from 10,000 centipoise (cps) to about 30,000 cps as a resting solid, or from 3,000 cps to about 10,000 cps as As used herein, the term "collagen" refers to the main protein of connective tissue that has a high tensile strength and that has been found in most multicellular organisms.

The term "biomaterial" refers to a material derived from a natural or synthetic source.

The term "bio ink" refers to an ink derived from biomaterial. Bio ink may include, but is not limited to, hydrogel. Hydrogel may include, but is not limited to, alginate, agarose, collagen, chitosan, fibrin, hyaluronic acid, carrageenan, polyethylene oxide, polypropylene oxide, polyethylene oxide-co-polypropylene oxide, hydroxypropyl methyl cellulose, poly(propylene fumarate-co-ethylene glycol), poly(ethylene glycol)-co-poly(lactic acid), poly(vinyl alcohol), KDL1 2 oligopeptides, and poly(n-isopropyl acrylamide). The hydrogels preferably have a controlled rate of crosslinking through the adjustment of environmental variables including, but not limited to, temperature, pH, ionic strength, heat, light, or the addition of chemical crosslinking agents such as calcium, magnesium, barium, chondroitin, sulfate, and thrombin.

3D structures may be fabricated from bio gels which are formed from collagen-based materials. Methods of harvesting collagen for use in bio gel compositions, bio gel compositions, methods for making 3D structures using bio gel compositions, and methods for preparing bio gel compositions for use in 3D printing systems are described in PCT Application Serial No. PCT/US2018/034582 entitled "3D PRINTABLE BIO GEL AND METHOD OF USE," filed on May 25, 2017, the entire contents of which are hereby incorporated by reference for the background information and methods set forth therein.

In one aspect, disclosed herein is a system for printing using biomaterial, wherein the system comprises a disposable barrier enclosing a printing surface and an assembly comprising a plurality of movable arms, wherein the plurality of movable arms comprises an upper arm coupled to a lower arm configured with an extruding system, wherein the extruding system comprises a syringe configured to deposit biomaterial, including but not limited to collagen-based biomaterial.

In one aspect, the biomaterial may be a bio ink comprising collagen, neutralizer and cellular media. Exemplary neutralizers include, but are not limited to, formulations containing weak acid, for instance. In some embodiments, the cellular media may include living cells which include, but are not limited to, epidermal cells, chondrocytes and other cells that form cartilage, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, or tracheal epithelial cells.

In another aspect, disclosed herein is a printer assembly including a "one time use" barrier and a "one time use" print bed on which material, e.g., biomaterial, is deposited. The barrier and/or print bed are disposable and, in at least one embodiment, are discarded after one use to avoid contamination. The printer assembly comprises a plurality of movable arms, including at least one movable arm which is configured to be inserted into a cavity (inlet) of the disposable barrier so as to be sheathed by the disposable barrier.

The systems and methods described herein allow for aseptic fabrication of structures by depositing material. As mentioned above, typical additive manufacturing systems have exposed parts that cannot be effectively aseptically cleaned. By way of example and not limitation, such exposed parts may include belts, pulleys, rails, bearings, lead screws, motors and wiring assemblies. Moreover, such systems may have surfaces which do not follow Good Manufacturing Practice (GMP) guidelines for aseptic cleaning capability or aseptic processing, as promulgated by the U.S. Food and Drug Administration, for example. In particular, such systems may have sliding components which cannot be sealed. Further, no barrier is provided between the printed construct and the printer itself. Additionally, conventional printers include numerous components requiring lengthy machine set-up times, which may delay printing operations once the biomaterial is prepared for printing (e.g., once collagen, neutralizer and cell media are mixed together).

In contrast, as described below, exemplary embodiments of the present disclosure achieve aseptic conditions in compliance with GMP guidelines, and allow for movable printing components to be sheathed in a protective barrier. In at least one embodiment, the printer system may be placed in a clean hood in which air is sterilized, for example, via a high efficiency particulate air (HEPA) filter. In at least one embodiment, the clean hood sterilizes air through the HEPA filter, and blows a portion of the sterilized air downward. The air flow of the sterilized air is such that a portion of the air blown downward may remain in the clean hood, while another portion may be discharged from the front opening of the clean hood. The printing system of at least one embodiment may be provided in the clean hood without disrupting the laminar air flow, thereby avoiding degradation of the aseptic environment. In at least one embodiment, a biosafety cabinet (BSC) may be used instead of a clean hood.

System Overview

Turning now to FIG. 1A, a perspective view of a system according to an embodiment is shown. The system is a printer assembly including a housing 101 and a print bed or stage 111 on which biomaterial may be deposited from a printing tip (a deposition tip), as discussed below in more detail. The height of the stage 111 may be measured by a tip height mechanism 110, as may also be referred to as a tip height setter, for determining where the stage 111 is positioned relative to the deposition tip.

Figure 1B:
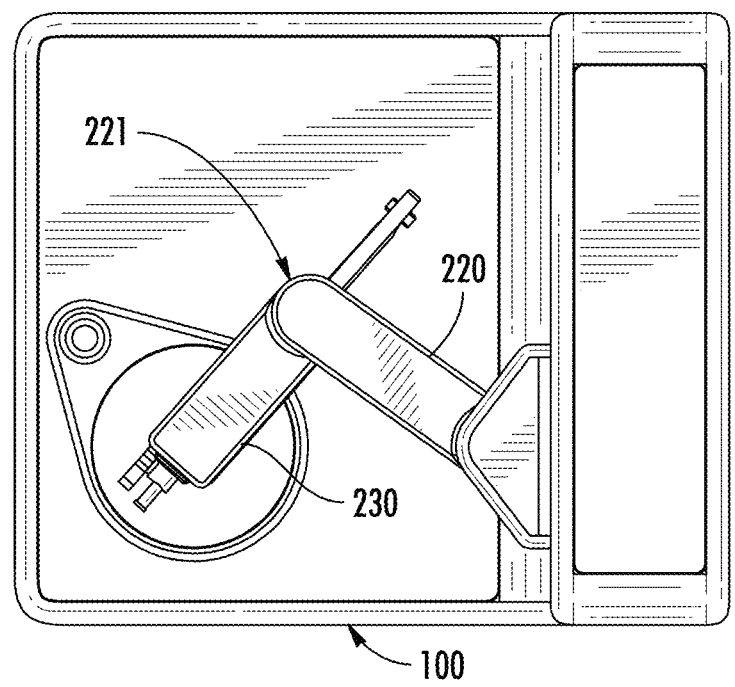
FIG. 1B is a top view of a system according to an embodiment.

FIG. 1B is a top view of a system according to an embodiment. As seen in FIG. 1B, above the stage 111 is an arm assembly including an upper arm 220 and a lower arm 230. The upper arm 220 and the lower arm 230 are connected by at least one component, including an elbow joint 221 that allows the lower arm 230 to move relative to the upper arm 220. The elbow joint 221 is formed so as to be staggered between upper arm 220 and lower arm 230, which are at different heights and are not co-planar. Elbow joint 221 allows for folding of the arms 220, 230, so as to increase a range of motion thereof.

In at least one embodiment, the elbow joint 221 acts as a hinge allowing for extension of the lower arm 230 to reach a plurality of positions, including a plurality of locations above stage 111. The stage 111 is a print bed configured to move along the z-axis, whereas the upper arm 220 and lower arm 230 are configured to move in the x-y plane. In some embodiments, the print bed may be heated, e.g., by heater 108. In at least one embodiment, the stage 111 is formed as a circular or ovoid disc. In at least one embodiment, the stage 111 includes at least a triangular portion and a semi-circular portion.

Figure 1C:
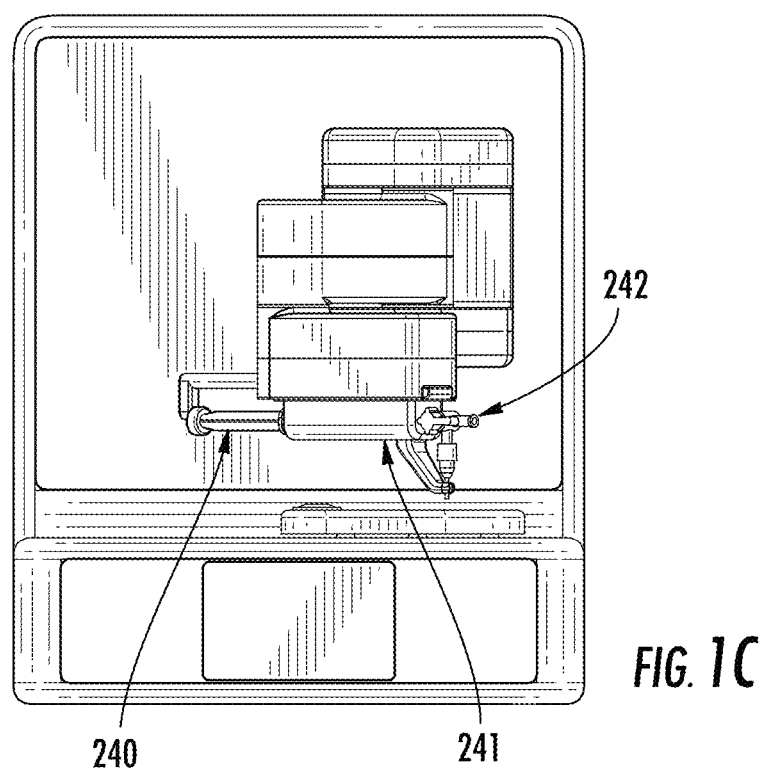
FIG. 1C is a front view of a system according to an embodiment.
Figure 1D:
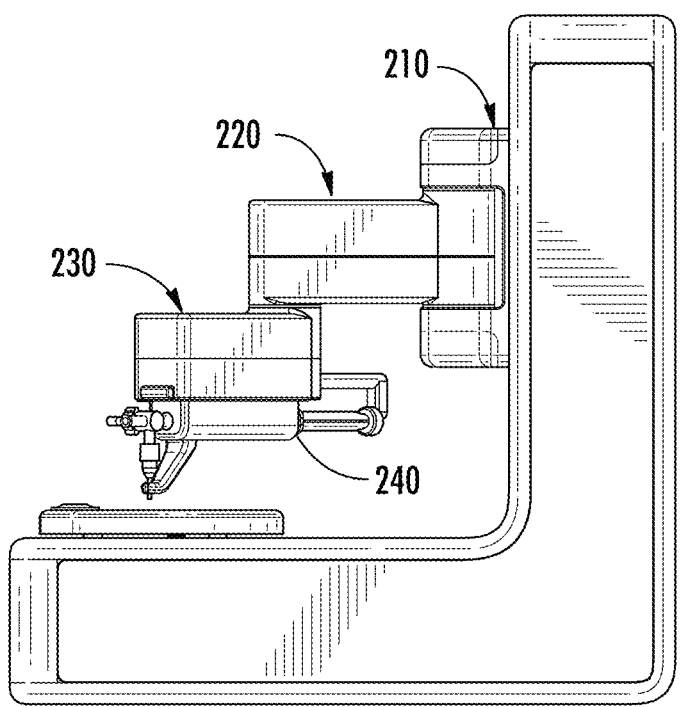
FIG. 1D is a side view of a system according to an embodiment.

FIG. 1D is a side view of a system according to an embodiment. FIG. 1D shows components including those depicted in FIG. 1B. In particular, the stage 111, lower arm 230 and upper arm 220 may be provided in a tiered or staggered arrangement. That is, stage 111 may be provided closest to a first end of housing 101 in a horizontal direction, and closest to a bottom of housing 101 in a vertical direction. The lower arm 230 may be provided in an intermediate location, above the stage 111 and positioned such that at least one end of lower arm 230 may be closer than stage 111 to a second end of housing 101 in the horizontal direction. The upper arm 220 may be provided at a location which is above stage 111 and lower arm 230, and closer to the second end of the housing 101 in the horizontal direction than to the first end of housing 101. Further, between the upper arm 220 and a second end of housing 101 in the horizontal direction, there may be disposed a shoulder joint 210 which regulates movement of upper arm 220. In addition, between the stage 111 and lower arm 230, additional components, such as an extrusion system including a plunger 240, may be disposed. The plunger 240 is provided with syringe 245, discussed below in more detail.

FIG. 1C is a front view of a system according to an embodiment. In the embodiment shown in FIG. 1C, system components, including those mentioned above, such as the upper arm 220, lower arm 230, elbow joint 221, tip height setter 110, and stage 111, for example, are sheathed by a barrier 285 so as to be enclosed therein and isolated from the outside environment. In some embodiments, a lower boundary of barrier 285 may extend to encompass a portion of housing 101 or may extend so as to completely encompass the printer assembly including housing 101. In some embodiments, a lower boundary of barrier 285 may coincide with an upper surface of a portion of housing 101.

Within the barrier 285, and thus protected from the outside environment, are components which may contact biomaterial directly or indirectly, and components adjacent to or connected directly or indirectly with such components. For example, inside barrier 285, there may be disposed an extrusion system as discussed below in more detail.

While the system shown in FIG. 1D, as with FIGS. 1A and 1B, do not depict barrier 285 shown in FIG. 1C, it should be appreciated that barrier 285 may be provided in some embodiments, e.g., by placing barrier 285 above an uppermost surface of housing 101 so as to envelop a printer assembly therein. The barrier 285 may be a disposable barrier which is replaced after the printer is used. For example, the barrier 285 may be replaced after a given number of 3-D fabricated structures are produced, after a predetermined quantity of biomaterial has been deposited by the syringe tip on stage 111, or after a predetermined length of time, or based on alternative factors or a combination of factors including but not limited to the foregoing. In some embodiments, barrier 285 may be biodegradable and/or recyclable. Although in certain embodiments, barrier 285 is discarded after one use, the barrier may be reused, e.g., after a sterilization process. Barrier 285 thus allows for components sheathed within to be protected from the outside environment, in furtherance of creating aseptic conditions conducive to fabrication of 3D biomaterials which may have tissue engineering implementations. In at least one embodiment, barrier 285 and all other polymer components of the printer assembly are made of virgin plastics according to USP Class VI and ISO 10993 standards and which withstand gamma ray sterilization. In at least one embodiment, all materials (e.g., polymer and non-polymer materials) are FDA approved. In at least one embodiment, the barrier may be substantially impermeable. Barrier 285 may be formed as a glove or sleeve encasing its contents.

In some embodiments, the barrier 285 may be first sealed with components placed inside, and thereafter sterilized, e.g., via gamma rays, an autoclave, via ethylene oxide gas, UV light exposure, or with one or more sterilizing chemical compositions, such as bleach formulations. Following fabrication, all items may be disposed of once the printed construct has been removed from the barrier 285 for post-printing processes (e.g., incubation). Prior to mixing of ink containing collagen, neutralizer and cell media, the printer arms are assembled with the barrier 285. In at least one embodiment, operations that are performed prior to mixing include 'homing' of the machine axis of the printer assembly, to ensure proper positioning, inflating the barrier 285, positioning the barrier 285 over the printer arm and the printer bed, and attaching the barrier 285 to the housing. Following attachment of the barrier 285 to the housing, the printer bed and extruder shaft are positioned in preparation for fabricating 3-D structures on the printer bed. An empty syringe is positioned in the barrier, and a position of a stopcock is adjusted to receive a flow of material (e.g., biomaterial) for printing. The temperatures of the printer bed and printer arm are allowed to equalize, in at least one embodiment. More specifically, the printer bed 111 is heated up prior to printing, while the printer arm is cooled. Next, a port, discussed below in more detail, is readied in order to receive the biomaterial.

In this manner, the printer assembly may be fully assembled prior to mixing, thus reducing the risk that time is lost for carrying out assembly steps once the ink has already been mixed. Further, the printer assembly is completed before mixing so as to allow for thermal equilibrium of the print surface and thermal equilibrium of a syringe housing to be attained. In at least one embodiment, the collagen, cellular media and neutralizer may be provided in a disposable enclosure forming an additional physical barrier. Further, in at least one embodiment, the printer assembly may be equipped with a plurality of sensors, including one or more of (1) a thermistor in at least one of a print bed or a print arm, to measure system temperature, (2) a pressure sensor configured to measure a pressure within the barrier, (3) a switch and/or position sensor, e.g., a limit switch, to limit displacement of any or all of the print bed, the printer arm, or the extruder system, and/or position sensors to provide 'homing' of any or all of the aforementioned components to ensure that they are in desired locations, (4) one or more encoders to provide closed-loop feedback on one or more motors of the system, and (5) positional sensors to detect positions of one or more of a syringe tip and a stopcock to determine correct alignment and installation. Further, in at least one embodiment, additional sensors may be provided, such as coolant sensors to measure a temperature and/or level of cooling fluid, and an air flow sensor to measure air flow within the system.

In at least one embodiment, the biomaterial may be maintained at a suitable temperature after providing it to a printer assembly of at least one embodiment herein, and specifically, by keeping syringe housing 241 at a controlled temperature. In some embodiments, the biomaterial is maintained at a temperature of about −20° C. to about 15° C. The temperatures may include, but not limited to, about −15° C. to about 10° C., about −10° C. to about 10° C., about −5° C. to about 10° C., about 0° C. to about 10° C., about 2° C. to about 8° C., about 2° C. to about 6° C., about 2° C. to about 5° C., about 2° C. to about 4° C., about 3° C. to about 6° C., about 3° C. to about 5° C., and ranges between any two of these values or less than any one of these values. In certain embodiments, the maintaining may include, but is not limited to, temperatures of about 2° C., about 3° C., about 4° C., about 5° C., about 6° C. and ranges between any two of these values or less than any one of these values. In one embodiment, the biomaterial is maintained at a temperature of about 4° C. In at least one exemplary embodiment, the cooling mechanism may comprise one or more of (1) a thermoelectric cooling system or (2) a cooling circuit configured to circulate cooled fluid through a heat transfer block.

Figure 1E:
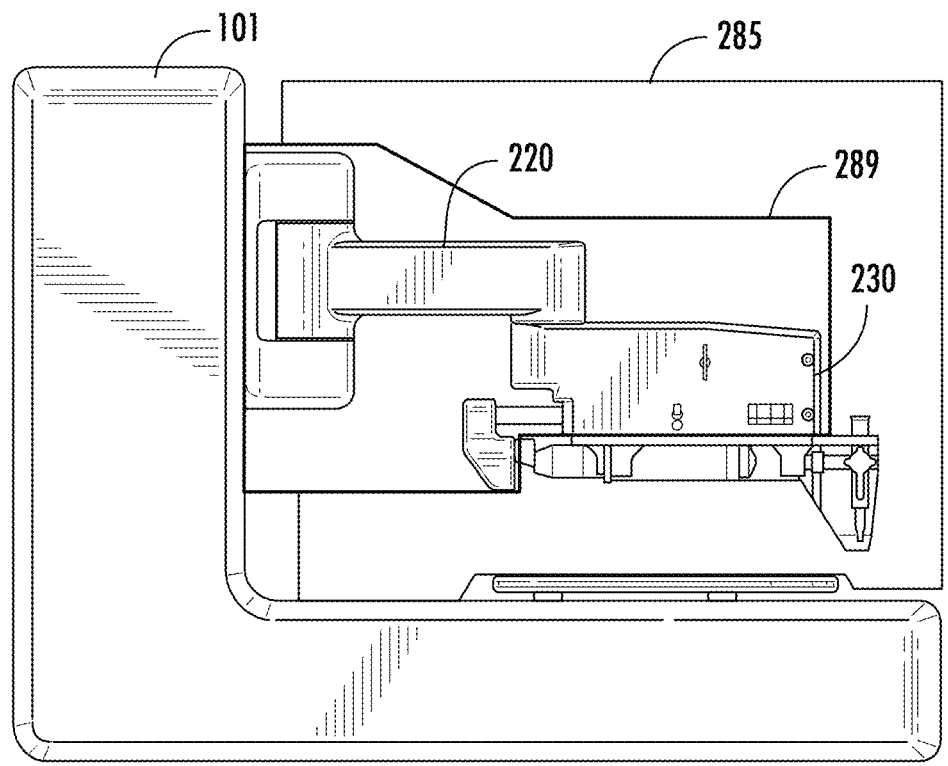
FIG. 1E is a side view of a system according to an embodiment.

FIG. 1E is a side view depicting barrier 285 as a substantially rectangular or cuboid shape having a perimeter which aligns with a perimeter of the housing 101. As shown in FIG. 1E, the barrier 285 may be provided together with an inlet 289, as may also be referred to as an inlet portion, which acts as a barrier between the arm assembly of the printer, such as shoulder joint 210, upper arm 220 and lower arm 230, and stage 111. In this manner, components which would not typically be disposed or replaced, such as upper arm 220 and lower arm 230, are isolated from the fabricated structures created on stage 111. Together, upper arm 220 and lower arm 230 form a dual arm system of the printer assembly which allows for rotational planar motion that translates to rectilinear motion of the tip of syringe 245.

Figure 1F:
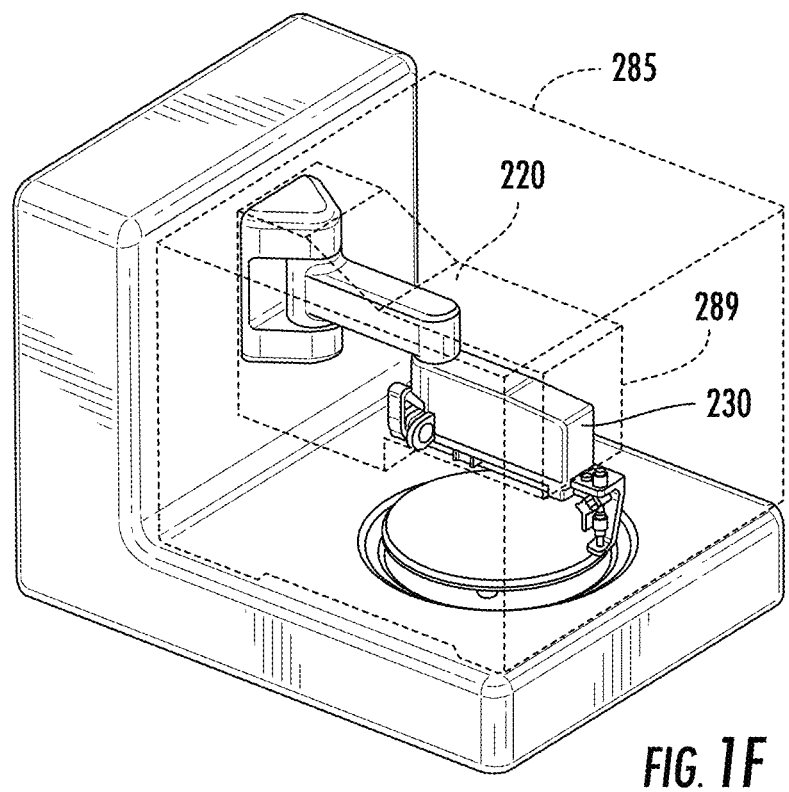
FIG. 1F is a perspective view of the system shown in FIG. 1E.

FIG. 1F is a perspective view of the system shown in FIG. 1E, including inlet 289 encasing the upper arm 220 and lower arm 230 and thus providing a barrier between the arm assembly and the syringe. Dual arm motion, e.g., of upper arm 220 and lower arm 230, is permitted within inlet 289, and freedom of motion of the upper arm 220 and lower arm 230 is not constrained by inlet 289. Thus, inlet 289 does not impede motion or extrusion capabilities of the printer assembly. Further, the inlet 289 allows for operation of the printer assembly without vibration or distortions from barrier 285. The barrier 285 including inlet 289 also does not disrupt laminar air flow within a clean hood in which the printer system may be situated for printing operations.

Chassis and Stage

Figure 2A:
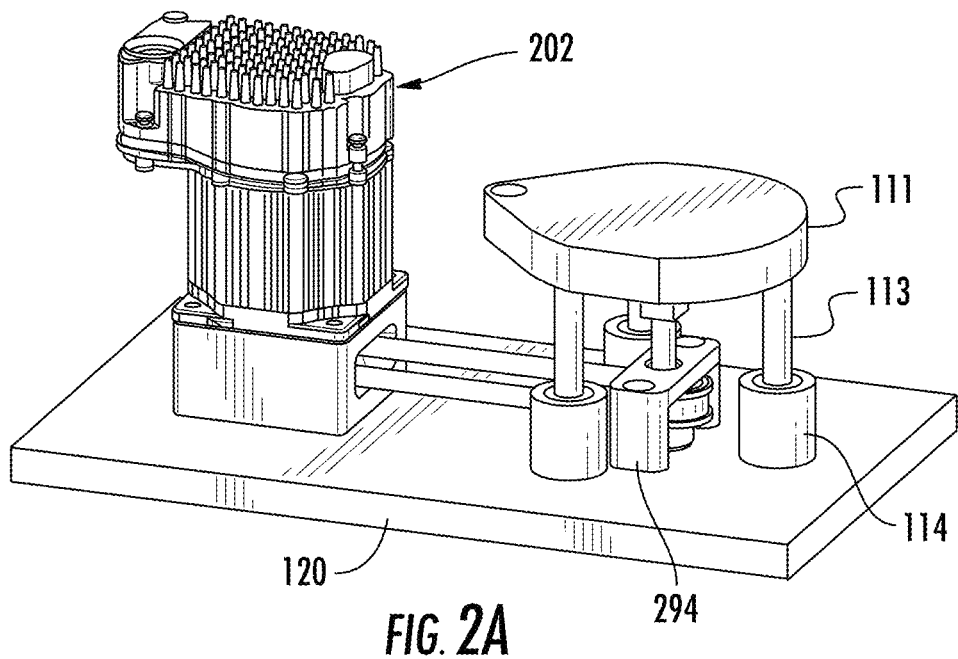
FIG. 2A is a side perspective view of a portion of a system including a motor assembly and a stage, according to an embodiment.

FIG. 2A is a side perspective view of a portion of a system including a motor assembly and a stage, according to an embodiment. As shown in FIG. 2A, the stage 111 is elevated above a plurality of guide pins 113. The guide pins 113 serve to provide structural support to stage 111 and to elevate stage 111 above chassis 120. Further, the guide pins 113 help to avoid rotation of stage 111 and maintain level and vertical movement thereof. In at least one embodiment, guide pin 113 prevents rotation of the stage 111 and ensuring that travel on the bed is linear and level. The guide pin 113 is configured to be arranged with bushings 114 provided concentrically around guide pin 113. The bushings 114 are coupled to the chassis 120, so as to mount stage 111 to chassis 120. Further, a central platform 294 is disposed at an approximate center of stage 111 on an underside thereof and is coupled to chassis 120. The central platform 294 includes at least one aperture which is dimensioned to accommodate lead screw 116. The platform 294 holds the pulley 117 in place. Motor 102 is configured to be coupled with drive belt 118 to effectuate driving of lead screw 116 in order to adjust a height of stage 111.

Figure 2B:
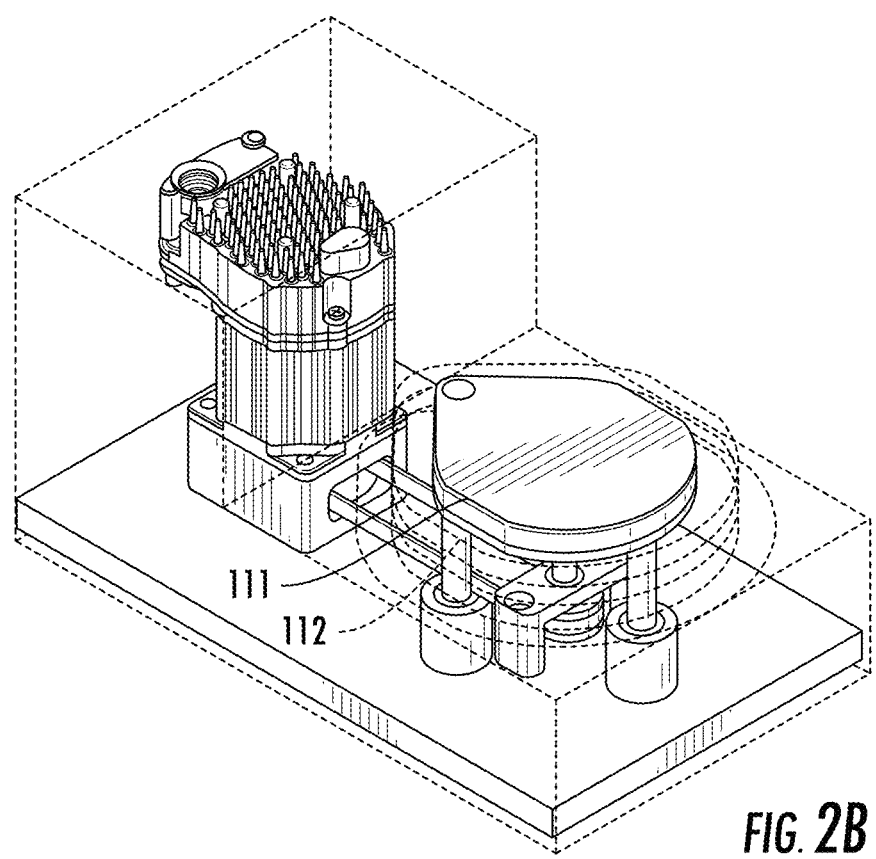
FIG. 2B is a front perspective view of a portion of a system including a motor assembly and a stage, according to an embodiment.

FIG. 2B is a front perspective view of a portion of a system including a motor assembly and a stage, according to an embodiment. As shown in FIG. 2B, housing 101 encases motor 102, chassis 120, platform 294, bushings 114 and guide pin 113, among other components. In addition to the components shown in FIG. 2A, the system of FIG. 2B further includes a skirt 112. Skirt 112 may be formed as an accordion structure which may expand or contract to adjust a height of stage 111 (e.g., by folding or compressing upon itself in response to a load on the skirt 112). The skirt 112 further isolates the aforementioned drive components from the aseptic environment within the clean hood. Further, skirt 112 may be arranged so as to be disposed between stage 111 and the housing 101.

Figure 2C:
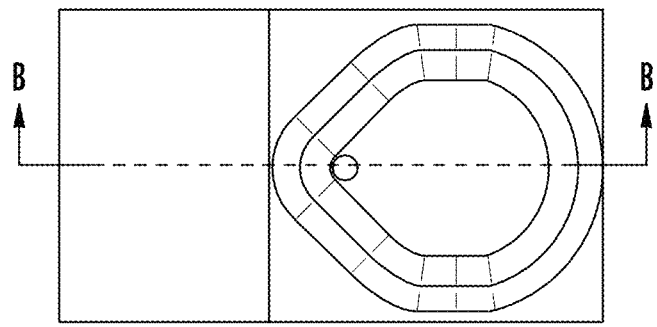
FIG. 2C is a cross-sectional view of a portion of a system including a motor assembly and a stage, according to an embodiment.

FIG. 2C is a cross-sectional view of a portion of a system including a motor assembly and a stage, according to an embodiment. As shown in FIG. 2C, skirt 112 may be constructed such that an outermost edge of skirt 112 is offset from an outermost edge of stage 111. The skirt 112 may contain a plurality of individual pleats. Further, the pleats of skirt 112 may sit above a skirt base which has a larger diameter than the pleats themselves, such that a radius of the pleats of skirt 112 is greater than a radius of the stage 111 but smaller than a radius of the skirt base. In at least one embodiment, the skirt 112 may be composed of one or more pliable materials including, but not limited to, polymer, rubber, silicon, composite materials, and thin metals. Such exemplary pliable materials may be aseptically cleaned in accordance with GMP standards.

Figure 2D:
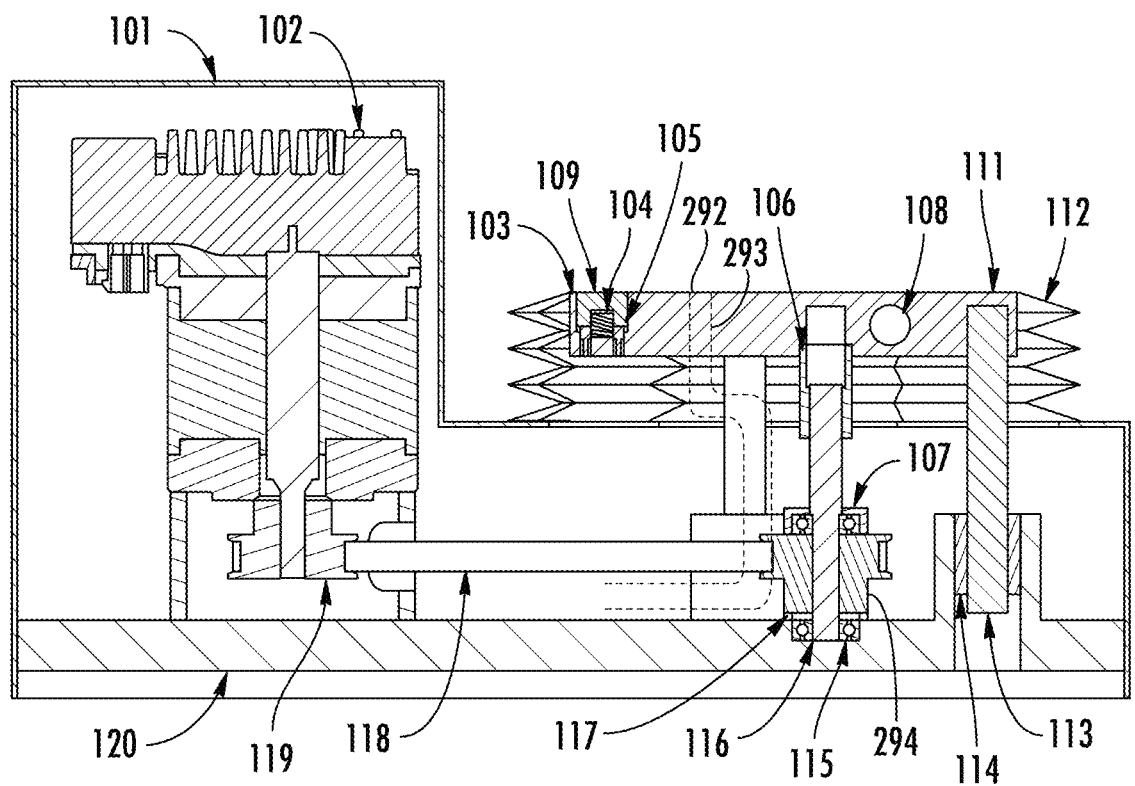
FIG. 2D is a cross-sectional view of a system including a motor assembly and a stage, according to an embodiment.

FIG. 2D is a cross-sectional view of a system including a motor assembly and a stage, according to an embodiment. As shown in FIG. 2C, housing 101 extends from a first end to a second end of the system in a horizontal direction, as also shown in FIG. 2B, for example. At the first end of the housing 101, motor 102 is disposed. In at least one embodiment, motor 102 may be a stepper motor that is a brushless DC motor. Motor 102 is disposed above chassis 120 and is configured to be coupled to a pulley 119. The pulley 119 of stepper motor 102 is configured to support movement of belt 118 along a circumference thereof.

Referring again to FIG. 2D, the belt 118 is a belt used to control movement of stage 111. In particular, belt 118 is coupled to a second pulley, pulley 117, which is communicated with stage 111 via lead screw 116. The lead screw 116 is arranged so as to abut against chassis 120, and is positioned with bearings 115 (e.g., ball bearings) concentrically arranged around lead screw 116 at a lower end of lead screw 116, which may be externally threaded. Another pair of bearings is disposed on left and right sides of lead screw 116 between the lower end of lead screw 116 and the upper end of lead screw 116. The bearings may be located, for example, so as to abut an upper surface of pulley 117. Further, at the upper end of lead screw 116, a drive block 106 may be positioned. The drive block 106, which may be internally threaded, serves to translate the rotational motion of the lead screw 116 into the linear motion of the stage 11. Bearings 115 restrict movement of the lead screw 116. The bearings 115 are provided in one or more retainers 107 disposed at upper and lower portions of platform 294 structured to retain lead screw 116 and pulley 117.

Referring again to FIG. 2D, at a second end of housing 101, bushing 114 is provided a guide pin 113. The bushing 114 is disposed concentrically around guide pin 113 at a base portion thereof. Guide pin 113 projects upward from bushing 114 so as to extend past an uppermost surface of bushing 114. An opening in housing 101 allows for guide pin 113 to pass through and extend beyond a surface of housing 101 to contact stage 111. In at least one embodiment, stage 111 may be provided with an opening at a lower side thereof to receive guide pin 113. The guide pin 113 may be dimensioned such that a height of the guide pin is less than a height of the skirt 112 when expanded.

Further, in at least one embodiment, as shown in FIG. 2D, the stage 111 may include one or more vacuum ports 292 at an upper surface of the stage 111. Each of the ports 292 may be, for example, a cylindrical aperture which is configured to receive a hose 293. The hose 293 may be fitted through a vacuum plate provided at the surface of the stage 111 in the vicinity of port 292. The hose 293 may be used to generate a vacuum (negative pressure) to hold a dish or another element in place by suction. For example, a vacuum may be established to secure a printing dish, a petri dish, a tissue culture dish, a flat material, or a walled container made of a material such as one or more of a plastic, glass, or metal, a composite material, or any combination of the foregoing.

Further, in at least one embodiment, a dish or material such as those described above may be attached to the stage 111 without a vacuum. For example, in certain embodiments, a sterile temporary adhesive may be employed to attach a printing dish, a petri dish, a tissue culture dish, or the like, to the print bed. In yet another embodiment, electrostatic charges may be employed to hold a printing dish in place. For example, by applying opposite electrostatic charges to the stage 111 and the printing dish, the printing dish may be held in place.

Additionally, in at least one embodiment, at a portion of stage 111 between lead screw 116 and motor 102, a contact assembly may be provided between the end of stage 111 and skirt 112. The contact assembly includes a pad 109 disposed above a spring 104. The spring 104 is an elastic member which is provided with a seal member 103 such as an O-ring, and contacts 105. The pad 109 may be a member such as a "touch off" pad which completes a circuit between contacts 105 when depressed by a tip 247 of syringe 245, i.e., in response to a load of the tip 247 on the pad 109. In another embodiment, a pressure-sensitive transducer may be provided under pad 109 which detects contact by tip 247 for 'homing' of the tip 247. Such a system may provide a confirmation that the tip 247 has been positioned correctly, and more particularly, that the bottom of the tip 247 has been positioned correctly in relation to the top of the stage 111. In at least one alternative embodiment, a probe pad is not used to check the height of tip 247. Rather, the whole bed may be moved under pressure to an indicated tip height or position. By checking different points on the bed, a level plane may be mapped out. If the stage 111 is tilted, the tilt can be compensated for by a control program used to operate a controller of the printer (discussed in more detail below).

Further, in at least one embodiment, the system is configured to determine whether the deposition tip 247 is primed, prior to printing. In particular, a load cell may be used to determine whether the deposition tip 247 is primed. Such a determination may be made by touching off the load cell in a similar manner as may be used to set the height of the tip 247 relative to the print bed. More particularly, printing material (such as biomaterial) may be deposited on the load cell, thereby placing a mass on the load cell itself, to confirm that material is present in the tip 247.

Referring again to FIG. 2D, the stage 111 is located at a portion of housing 101 which is lower than a portion of housing 101 in which motor 102 is disposed. Along part of this lower portion of housing 101, the skirt 112 is provided between housing 101 and stage 111. Additionally, a heater 108 may also be provided. In at least one embodiment, the heater may be a cartridge heater, a silicon heater, a ceramic heater, or a Kapton® (polyimide) heater, for example. The heater is configured to heat the print surface to achieve or maintain desired conditions conducive to formation of a printed construct, for example. In certain embodiments, the heater 108 is configured to maintain the print bed at a desired temperature range. The heater 108 may be configured to maintain the print bed at a temperature at which a gelation rate of the bio material may be maximized, for example. The temperature range may be, but is not limited to, about 25° C. to about 37° C., about 27° C. to about 35° C., about 30° C. to about 33° C., and ranges between any two of these values or less than any one of these values. Suitable temperatures may include, but not limited to, about 25° C., about 27° C., about 30° C., about 32° C., about 35° C., about 37° C. and ranges between any two values or less than any one of these values, for example.

Extruding System

Figure 3A:
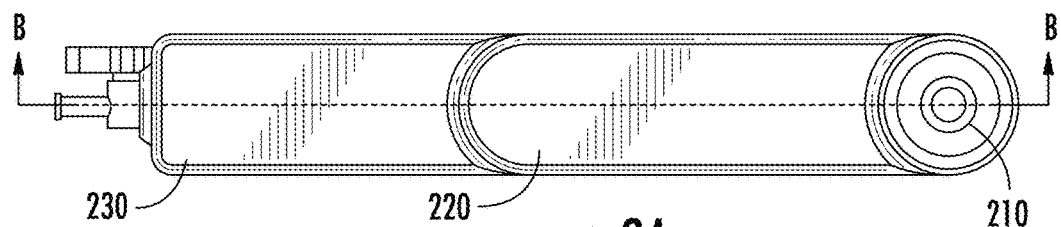
FIG. 3A is a top view of a portion of a system according to an embodiment.
Figure 3B:
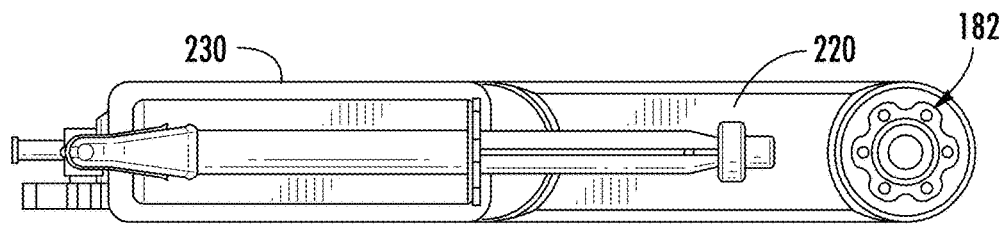
FIG. 3B is a top cross-sectional view of a system according to an embodiment.
Figure 3C:
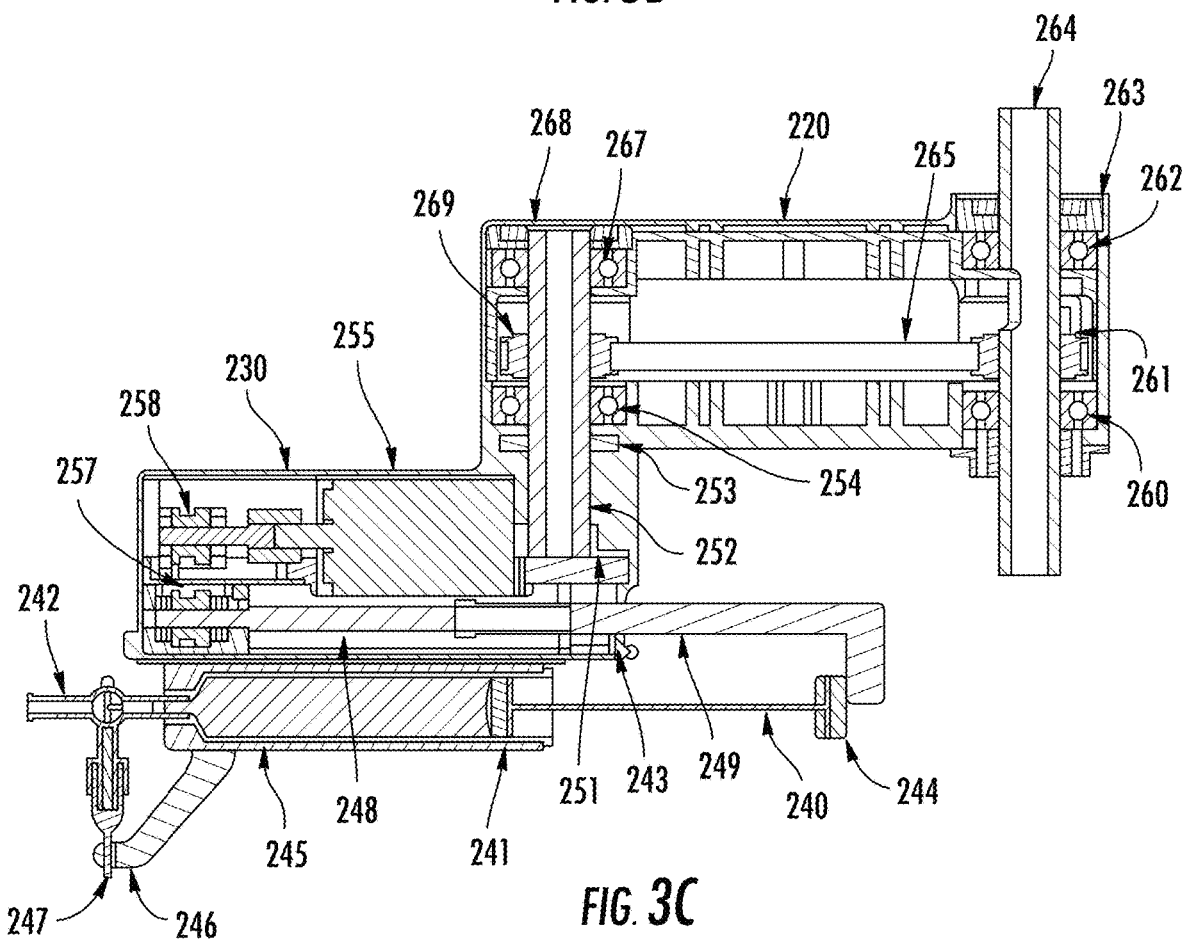
FIG. 3C is a cross-sectional view of a system including an extruding system according to an embodiment.

FIG. 3C is a cross-sectional view of a system including an extrusion system according to an embodiment. The extruding system comprises a plunger, plunger actuator and syringe components, together with a valve to regulate a direction of the flow of the biomaterial, as discussed below.

The extruding system is provided with lower arm 230. As shown in FIG. 3C, motor 255 is provided to effectuate movement of extruder components connected to lower arm 230, in addition to a pair of pulleys 257, 258. Pulley 258 is an actuator motor pulley which transmits power between motor 255 and pulley 257. Pulley 257 is a lead screw pulley which transmits power between motor 255 and lead screw 248. A belt driven by motor 255 links pulleys 257, 258, the lower pulley 258 causing the lead screw 248, which has external threads, to rotate. In response to a signal (e.g., from a programmable controller), motor 255 is configured to turn lead screw 248 so as to control movement of the syringe 245 by actuating plunger 240 via plunger actuator 249.

The extrusion system includes plunger 240, a syringe housing 241 for a syringe 245 configured to contain biomaterial and to deposit the same on stage 111, and a valve 242. Syringe 245 may be a reciprocating pump including the plunger 240, which fits within housing 241. The plunger 240 may be linearly pulled and pushed along the inside of housing 241, allowing the syringe to take in and expel biomaterial through a discharge orifice at a front (open) end of the housing 241.

At a lower-left side of the system, tip 247 of syringe 245 is positioned. The tip 247 is configured to deposit biomaterial on the stage 111 (not shown). The tip 247 may be held in place and/or guided to a desired location (e.g., a specific position above the stage 111) by a tip locator 246. The tip locator 246 may be formed as an arm that projects downwardly from syringe housing 241 in a direction of the tip 247. Syringe housing 241 is disposed beneath a lead screw 248.

The plunger 240 may be mated to plunger actuator 249 via a coupler, after biomaterial is loaded therein. The actuator 249 is adjacent to and abuts against an O-ring 243. The O-ring 243 serves to provide vibration dampening and acts as a seal between the internal printer environment and the aseptic barrier environment. The plunger 240 is disposed beneath the actuator 249. While the actuator 249 and a coupler between the actuator 249 and syringe are not enclosed in the arms 220, 230, they are nevertheless isolated from the printed construct by barrier 285. Further, the plunger 240 is provided with a plunger head 244 at an end of the plunger 240 which is opposite from deposition tip 247. A coupler is provided to attach the plunger head 244 to the shaft of the extruder.

The lead screw 248 drives the actuator 249, which is internally threaded, to act as a force on plunger head 244. Thus, a threading connection between lead screw 248 and actuator 249 is established. In this manner, rotation of the lead screw 248 moves the plunger actuator 249 in and out of lower arm 230, thereby causing the plunger 240 to move so that biomaterial is pumped out through valve 242 to tip 247. Further, as movement of the syringe 245 is driven by actuator 249, the syringe is not provided with a plurality of components to effectuate movement that are concentrated at the tip 247. That is, the extruding system includes components distributed in an axial direction of the syringe, minimizing the mass located at the end of the lower arm 230. This is in contrast to systems in which a vertical extrusion unit is positioned with a tip at one end and extruding components positioned in a vertical arrangement relative to the tip (e.g., multiple components stacked atop the tip). Such vertical systems typically extend the center of mass farther from machine pivot points, thereby increasing vibrations on the system and inertia.

In at least one embodiment, valve 242 is a three-way stopcock which regulates flow of liquid (e.g., biomaterial) so as to start and stop flowing of biomaterial to the tip 247. The stopcock may be manually operated in at least one embodiment. Further, the stopcock may be used together with one or more position sensors to ensure proper alignment prior to printing.

Various alternative embodiments may be employed which may include or omit one or more of the syringe 245 and the plunger 240. For example, in at least one embodiment, the syringe 245 may be configured to receive biomaterial which is pressurized by a fluid (e.g., a gas or liquid), without provision of plunger 240. For example, pressurized fluid (such as sterile air or a non-compressible buffer medium, in at least one embodiment) may be directed into the syringe 245 at a first end of the syringe 245 which is opposite from a second end proximate to the deposition tip 247. The air pressure acts against the piston within the syringe to cause the piston to direct biomaterial downward and to expel the biomaterial through the deposition tip 247, for example. In at least one embodiment, the syringe is fitted with an end-cap against which the pressurized fluid acts, and the ink is expelled through a nozzle. One or more compressor pumps may be used to apply pressure to pressurize the fluid, at a constant or variable rate and/or at a pressure which is maintained to fall below a threshold pressure.

In one or more further alternative embodiments, the printer includes more than one syringe 245. For example, in at least one embodiment, two or three syringes may be mounted to an arm in the same manner as the single syringe 245 discussed above. Further, two or more of the syringes 245 may be plumbed together. For example, two or more syringes 245 may be joined so as to extrude from a common deposition tip 247; alternatively, each syringe 245 may be provided with its own separate tip. Further, the syringes may be extruded by coupling respective plungers 240 together to the motor of the lead screw 248. Additionally, in certain embodiments, one or more of a plurality of syringes 245 may be extruded by its own respective lead screw motor.

Further still, in at least one embodiment, an exemplary extruder may include a tube or hose and may omit the syringe 245. In at least one embodiment, the tube or hose may be segmented, with at least a first portion outside the barrier 285 and at least a second portion inside the barrier 285. In another embodiment, the tube or hose may be a continuous feed line. For example, a tube or hose may be inserted through one or more grommets, seals and/or ports, e.g., ports 3, 9 provided in and/or on barrier 285. As discussed below in greater detail, such ports may be fluid fittings providing leak-free communication from an outside of barrier 285 to an interior thereof. In such embodiments, the tube or hose is filled with pressurized biomaterial and directly supplies the pressurized biomaterial to the deposition tip 247. The biomaterial which is fed through the tube or hose to the deposition tip may be drawn from a reservoir. Additionally, in at least one embodiment, inkjet material deposition may be used to deposit the biomaterial on a substrate.

Moreover, in at least one embodiment, a valve other than or in addition to valve 242 may be employed, e.g., with the syringe 245 as configured with the plunger 240, and/or with the syringe 245 as configured to receive pressurized biomaterial without plunger 240, and/or with the tube or hose filled with pressurized biomaterial (i.e., without the syringe 245). Such a valve may allow for control of the flow of biomaterial to deposition tip 247. In at least one embodiment, the valve may be one or more of a pinch valve, a ball valve, a solenoid valve, a diaphragm valve and a needle valve.

Certain embodiments include mechanisms for verifying that deposition has been or is being performed correctly. For example, in at least one embodiment, a real-time verification may be performed to confirm that material has been deposited from the deposition tip 247 in an intended location. In at least one embodiment, verification may be performed using a verification instrument that may be one or more of a physical probe, a laser, a sonar signal, an ultrasonic signal, a stereo camera, or LIDAR, for example. In particular, a laser such as a single point laser, a line laser, or a 2-D laser array may be used to determine whether deposition has been or is being carried out in an intended manner. The verification instrument may allow for three-dimensional scanning of an article formed by deposition of material from the tip 247. For example, the verification instrument may be a line laser which is configured to detect and measure a profile of an object surface (e.g., a three-dimensional printed article).

By way of illustration and not of limitation, where the verification instrument is a physical probe, for example, the probe may employ the same drive mechanism as the printer. In at least one embodiment, the verification instrument may be mounted to a lower print arm 230 of a print arm assembly, which is discussed in more detail below. The verification may be performed during deposition or immediately thereafter, for example. Randomized verification may be performed to assess whether deposition is consistently occurring at one or more intended locations.

Arm Assembly Including Upper and Lower Arm

FIG. 3A is a top view of a portion of a system according to an embodiment. As shown in FIG. 3A, shoulder joint 210 is aligned with upper arm 220. Upper arm 220 may be positioned in the same axial direction as lower arm 230 so as to appear in a straight line when viewed from the top. FIG. 3B is a top cross-sectional view of a system according to an embodiment. As with FIG. 3A, in the cross-sectional view of FIG. 3B, the upper arm 220 and lower arm 230 are aligned so as to form a straight line. The upper arm 220 rotates freely about the shoulder joint 210. The lower arm 230 and elbow joint 221 rotate freely from the upper arm 220. A spline 182 is provided for upper arm 220 within shoulder joint 210. The spline is provided on an underside of upper arm 220. The spline 182 interfaces with a splined arm linkage of upper arm 220.

As mentioned above, elbow joint 221 is provided as a hinged connection between upper arm 220 and lower arm 230, while shoulder joint 210 is provided at upper arm 230. The elbow joint 221 is provided in an elbow joint shaft 252. Similarly, at the upper arm 220, a shoulder joint shaft 264 is disposed, in which the shoulder joint 210 is positioned. The shoulder joint shaft 264 rotates the pulleys 261, 269 which are linked by a timing belt. Opposite the shoulder joint shaft 264 is the elbow joint shaft 252, which is locked into collar 251. The collar 251 is a shaft collar mounted on lower arm 230 to transfer rotational motion of shoulder joint shaft 264 to lower arm 230. The shoulder joint shaft 264 and elbow joint shaft 252 are configured to spin freely relative to a plurality of ball bearings, as discussed below, and are held axially by a plurality of thrust bearings, as discussed below.

Above the actuator 249, collar 251 is provided around the elbow joint shaft 252. Elbow joint shaft 252 is further provided with elbow shaft pulley 269 at an upper portion thereof. Thrust bearing 258 is provided above elbow shaft pulley 269, and thrust bearings 253, 254 are positioned above collar 251. Ball bearings 267 are located concentrically with respect to elbow joint shaft 252 at axial side ends thereof. The shoulder joint shaft 264 includes ball bearings 260, 262 disposed at lower and upper portions of shoulder joint shaft pulley 261. Thrust bearing 263 is disposed above shoulder joint pulley 261 and ball bearing 262.

Figure 4A:
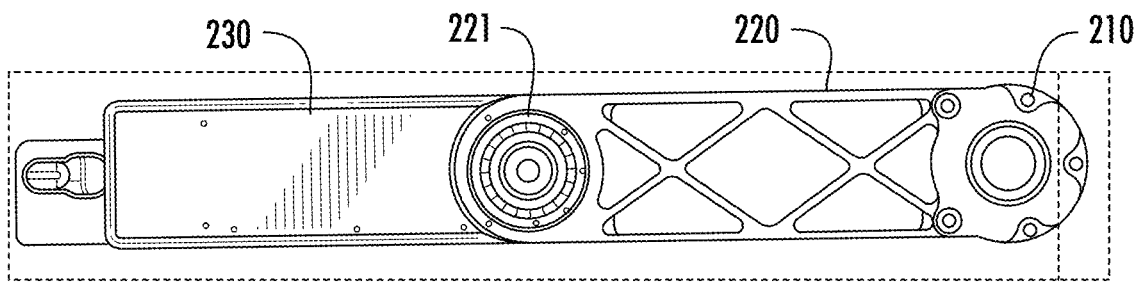
FIG. 4A is an exposed view of a portion of a system according to an embodiment.
Figure 4B:
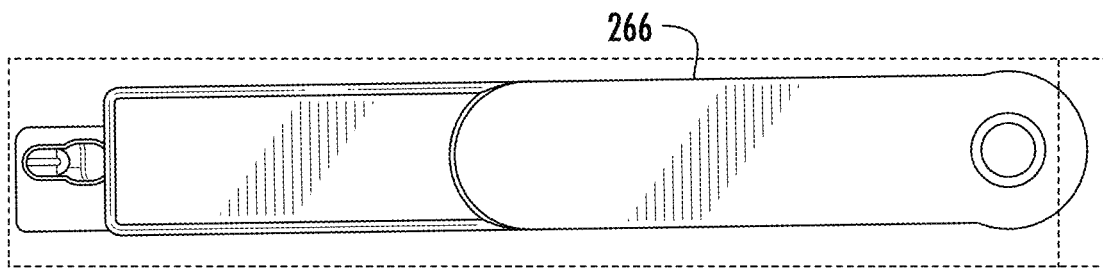
FIG. 4B is an exposed view of a portion of a system according to another embodiment.

FIG. 4A is an exposed view of a portion of a system according to an embodiment. As with FIGS. 3A and 3C, the upper arm 220 and lower arm 230 are aligned in an axial direction. Shoulder joint shaft 264 accommodates shoulder joint 210, while elbow joint shaft 252 accommodates elbow joint 221. At least one rotary seal is positioned on shaft 264 to further isolate an interior of the printer arm from the aseptic environment. In at least one embodiment, the upper arm may be provided with at least one latticed portion, allowing for weight reduction of the housing while achieving structural rigidity, as shown in FIG. 4A. In at least one embodiment, the upper arm may have a solid top shell 266, as shown in FIG. 4B. The shell 266 may be defined by smooth surfaces, e.g., smooth upper and lower surfaces, and formed of substantially non-porous material. The shafts 252, 264 form hollow passageways which provide one or more conduits for cooling fluid to flow to syringe housing 241, so as to establish fluid communication between the syringe housing 241 and a coolant source (e.g., a reservoir). Such cooling fluid promotes heat exchange in the system by thermoelectric cooling. For example, as mentioned above, in one embodiment, the biomaterial is maintained at a temperature of about 4° C. To keep the syringe housing 241 at such a temperature, hydraulic passages may be provided in one or more of shafts 252, 264 to deliver coolant to the syringe housing 241. Further, in at least one embodiment, the shafts 252, 264 may accommodate electrical wires which are threaded through the hollow spaces defined by the shafts, e.g., to route electrical wires to the motors 280, 299.

Figure 4C:
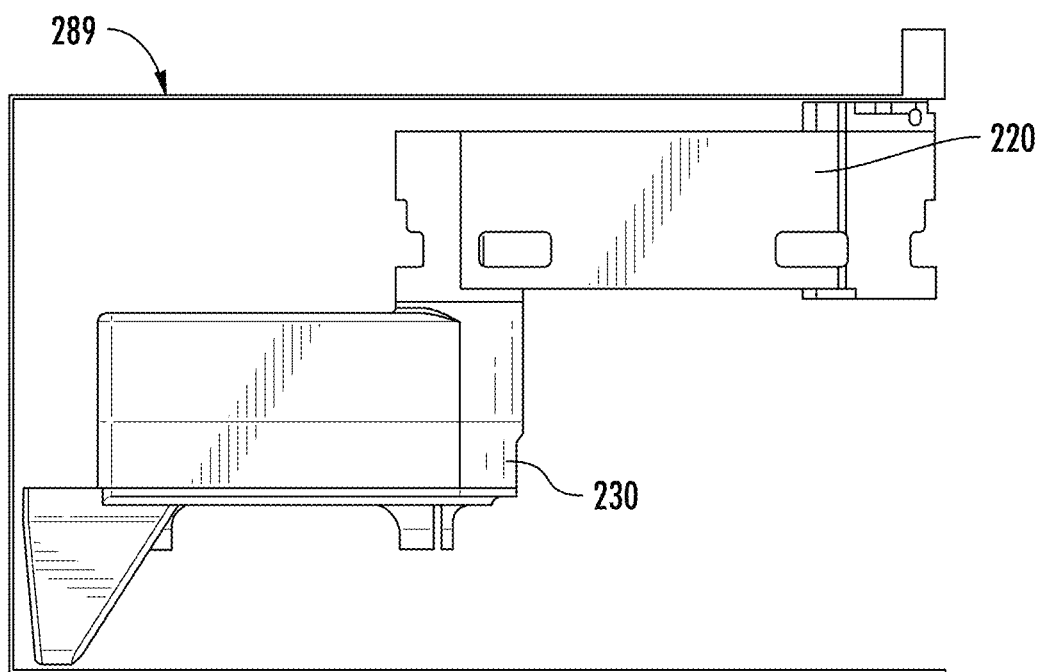
FIG. 4C is a side view of a portion of a system including a plurality of movable arms according to an embodiment.

FIG. 4C is a side view of a portion of a system including a plurality of movable arms according to an embodiment. The upper arm 220 and lower arm 230 are encased in inlet 289 of barrier 285 which acts to shield the arms 220, 230. Beneath the lower arm 230, the syringe 245 is loaded with biomaterial at a location within inlet 289. The syringe 245 is sheathed within inlet 289. Other components of the syringe, e.g., plunger 240, are provided within the inlet 289. Further, in at least one embodiment, barrier 285 attaches to housing 101 or chassis 120, e.g., via attachment tabs or clips 11.

In at least one embodiment, the distal portion of the arm assembly is covered by a disposable sheath. In at least one embodiment, only a portion of the upper arm 220 and/or only a portion of lower arm 230, and/or both of portions of or the entirety of the lower arm 220 and/or upper arm 230 may be covered by a disposable sheath. In this manner, the disposable sheath separates one or more portions of the arm assembly, or the entirety of the arm assembly, from the syringe.

Motor Drive and Arm Shafts

Figure 5A:
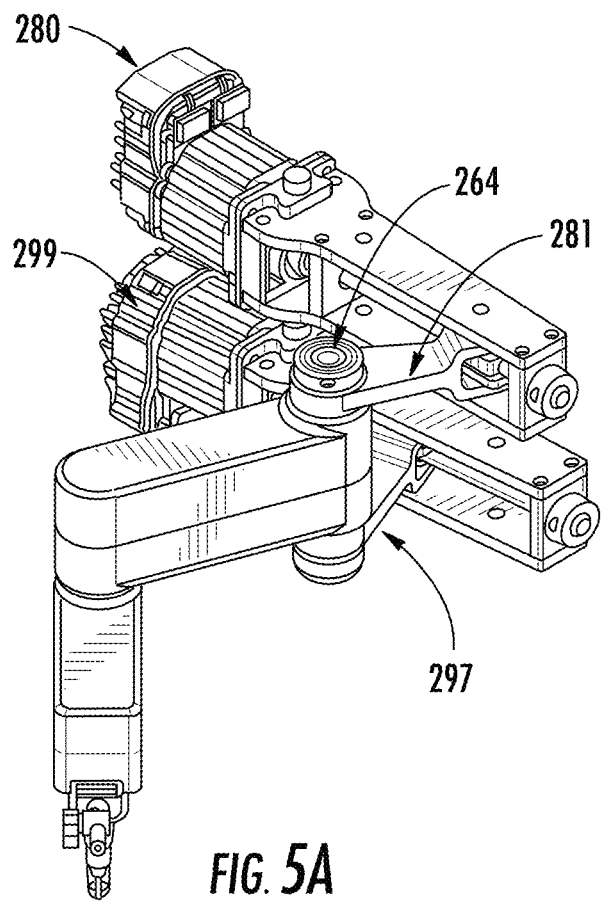
FIG. 5A is a first perspective view of a motor and arm assembly according to an embodiment.

FIG. 5A is a first perspective view of a motor and arm assembly according to an embodiment. The motor and arm assembly includes a first motor 280 and a second motor 299. First motor 280 is coupled to a first assembly including a first lead screw 282 coupled to shoulder joint drive shaft 264 via first linkage 281, to control driving of lower arm 230. Second motor 299 is coupled to a second assembly including a second lead screw 296 coupled to shoulder joint shaft 264 via a second linkage 297, to control driving of upper arm 220.

Figure 5B:
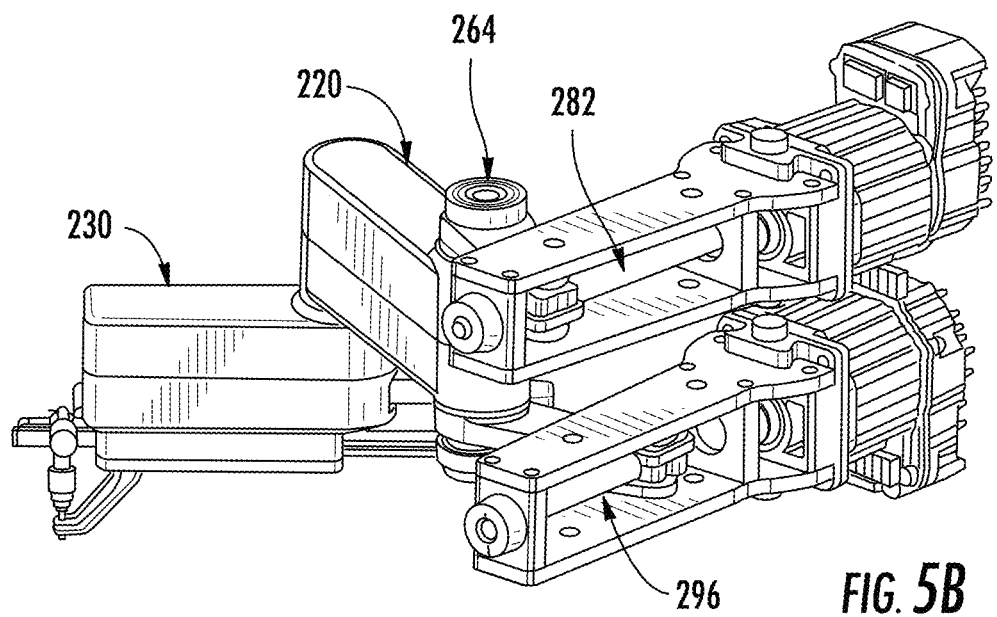
FIG. 5B is a second perspective view of a motor and arm assembly according to an embodiment.

FIG. 5B is a second perspective view of a motor and arm assembly according to an embodiment. FIG. 5B is a perspective view taken from an opposite side from FIG. 5A, with the arms 220, 230 being at a rear side. As shown in FIG. 5B, the construction of the first and second assemblies may be substantially similar, thereby allowing for a reduction in a number of unique parts. Further, by stacking the two motors 280, 299 with the first and second assemblies, the dual arm motion system may be realized in a compact footprint. Moreover, machine arm travel may be minimized over the fabricated structures (the printed constructs). Further, the belt 118 and pulleys 117, 119, 257, 258, 261 and 269 are provided in a sealed enclosure, thereby being further isolated from the aseptic environment established within the clean hood, allowing for aseptic cleaning. In at least one embodiment, all belts, motors, circuit boards, sensors and wiring assemblies are enclosed and sealed from barrier 285. The casings of these components are substantially smooth and non-porous, inhibiting ingress of foreign material.

Figure 5C:
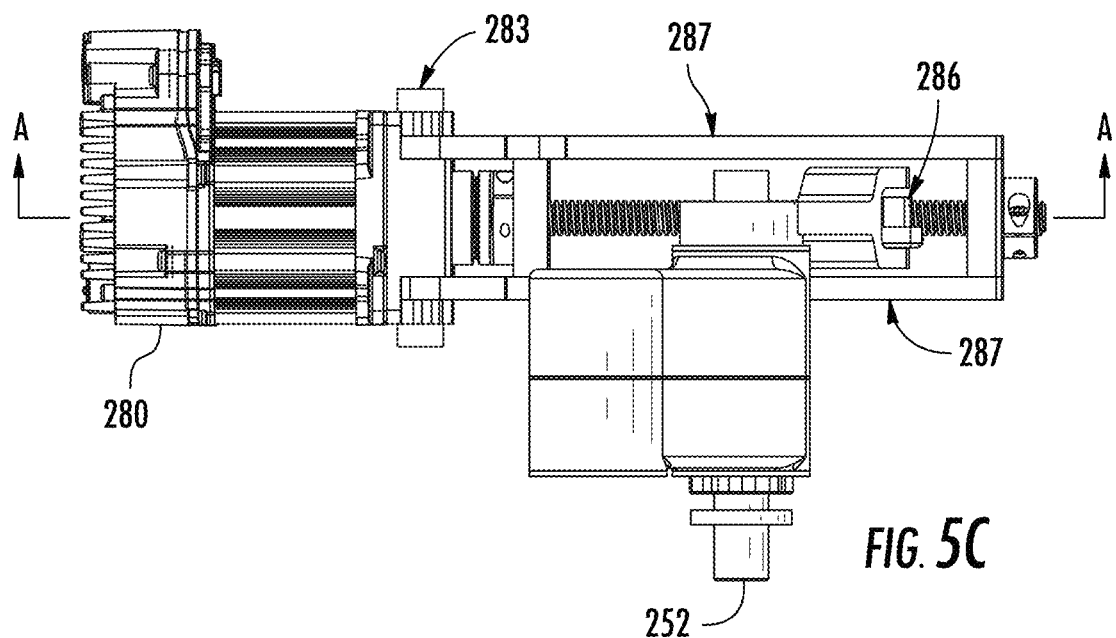
FIG. 5C is a first exposed view of a portion of a system including a motor drive assembly according to an embodiment.
Figure 5D:
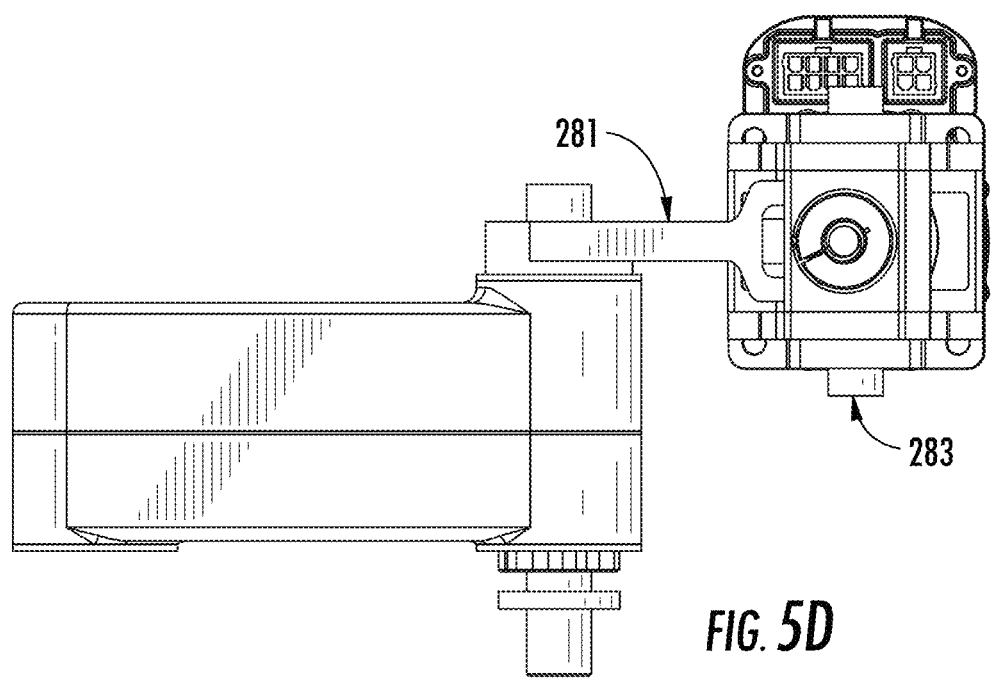
FIG. 5D is a second exposed view of a portion of a system including a motor drive assembly according to an embodiment.

FIG. 5C is a first exposed view of a portion of a system including a motor drive assembly according to an embodiment. In at least one embodiment, the motor drive assembly is has one or more casings which are substantially smooth and non-porous. In particular, FIG. 5C depicts motor drive components of upper arm 220. In FIG. 5C, motor 280 is disposed adjacent to a pivot 283, which may be a threadless axial pivot according to one or more embodiments. The pivot 283 allows rotation of the motor to a motor drive housing 287 and a housing of a lead screw 282. Inside the motor drive housing 287, a plurality of components may be accommodated. A lead screw nut 286 may be provided, for example, which is driven linearly along lead screw 282 as the motor turns the lead screw 282. Lead screw nut 286 may be attached to a linkage shaft around which linkages 281, 297 rotate. The elbow joint shaft 252 may be communicated with motor drive housing 287 to control movement of elbow joint 221. At least one rotary bushing is positioned on shaft 252. FIG. 5D is a second exposed view of a portion of a system including a motor drive assembly according to an embodiment. As seen in FIG. 5D, first linkage 281 may be provided between motor drive housing 287 and lower arm 230.

Figure 5E:
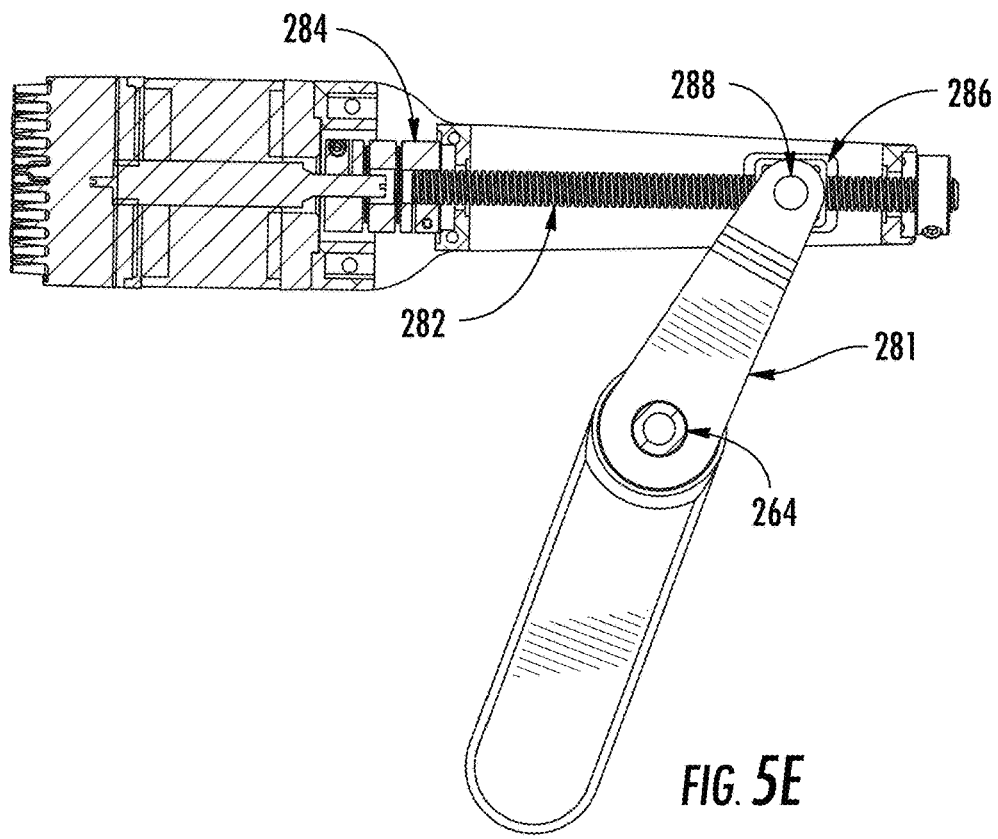
FIG. 5E is a cross-sectional view of a lower arm motor drive according to an embodiment.

FIG. 5E is a cross-sectional view of a lower arm motor drive according to an embodiment. The motor drive assembly of lower arm 230 may be similar to that of upper arm 220 described above. A coupler lead 284 may be positioned to couple motor 299 to lead screw 282. Linkage screw shaft 288 is configured to be communicated with lead screw 282, e.g., via screw nut 286. The linkage screw shaft 288 is connected to first linkage 281, which is communicated with the shoulder joint shaft 264 to be connected at joint 210. The motor 280 rotates around linkage screw shaft 288. In at least one embodiment, the linkage is configured to travel in an arcuate path about an axis of shoulder joint 210.

Figure 5F:
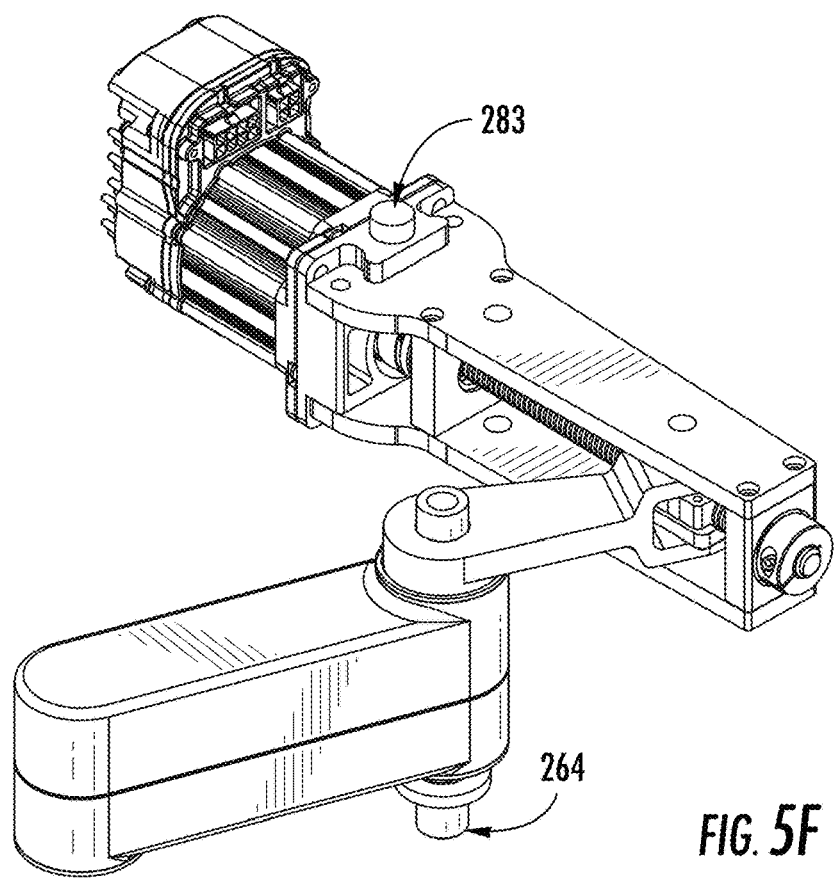
FIG. 5F is a perspective view of a portion of a system including a motor drive assembly according to an embodiment.

FIG. 5F is a perspective view of a portion of a system including a motor drive assembly according to an embodiment. As shown in FIG. 5F, the shoulder joint shaft 264 is configured to communicate with the first linkage 281 so as to respond to rotational motion of lead screw 282. The linkage 281 may include a claw at one end thereof, as seen from the top view in FIG. 5D. The claw may be dimensioned such that an upper prong of the claw may be attached above lead screw 282, while a lower prong may be attached beneath lead screw 282, the upper and lower tines fitting between the lead screw and respective upper and lower surfaces of motor drive housing 287.

As described above, the lead screws 282, 296 may be provided with the linkages 281, 297, such that the linkages 281, 297 are rotationally driven. In this manner, backlash in the system may be minimized as compared to systems which are belt driven. Further, greater acceleration in x-y plane directions may be achieved as compared to belt-driven systems. In particular, the lead screws carry out transmission of rotational energy by rotating, whereas the belt driven systems transmit power by movement of a belt over multiple pulleys, which generally takes longer. In some embodiments, the system may achieve accelerations of at least about 50,000 mm/s$^2$, about 50,000 mm/s$^2$ to about 60,000 mm/s$^2$, about 60,000 mm/s$^2$ to about 70,000 mm/s$^2$, about 70,000 mm/s$^2$ to about 80,000 mm/s$^2$, and ranges between any two of these values or less than any one of these values. In contrast, conventional Cartesian gantry systems may accelerate between about 3,000 mm/s$^2$ to 15,000 mm/s$^2$. Such systems cannot achieve sufficient travel accelerations to print biomaterial in a smooth, uniform fashion due to the shear-thinning characteristics of the material. The physical arrangement of the above-mentioned structures collectively forming the system, together with the power output realized by the abovementioned motors, contributes to the improved accelerations realized by one or more embodiments.

In one or more embodiments, an alternative drive mechanism may be used for the arm assembly discussed above, comprising an upper arm 220 and a lower arm 230, and/or for the print bed or stage 111. For example, the driving mechanism of each of the arm assembly and the stage 111 may include, but is not limited to, one or more of the following: cable drive systems, harmonic drive gears, non-captive linear actuators, electromagnetic motion systems, belt and pulley systems, direct drive linkages, pneumatic actuators and/or motors, hydraulic actuators and/or motors, rack and pinion drives, and lobed shafts which drive the cam linkages. Further still, in at least one embodiment, the motors may be directly connected to the linkage arms 281, 297, without the aforementioned driving lead screw 282, 296. Further, in at least one embodiment, the motors may be driven with a belt and pulley system, as mentioned above, or with a rack and pinion system. One or more of the aforementioned drive mechanisms may be used to raise or lower the stage 111 and/or effectuate movement of the arms.

Disposable Components

Figure 6A:
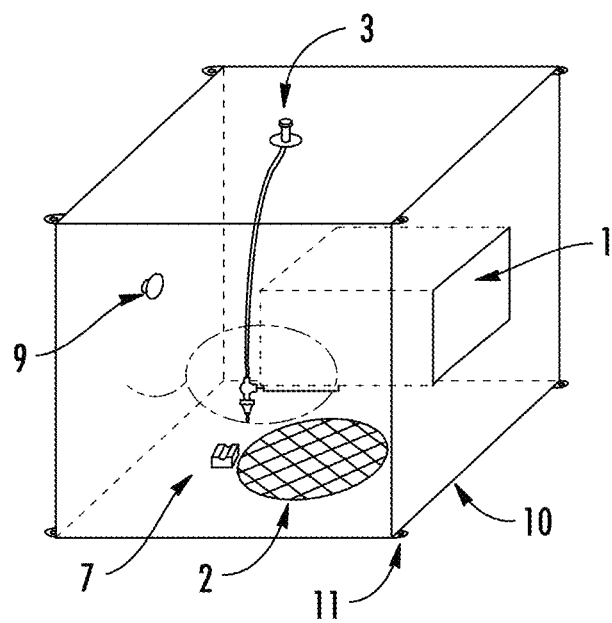
FIG. 6A is a perspective view of a portion of a system including a disposable barrier, according to an embodiment.

FIG. 6A is a perspective view of a portion of a system including a disposable barrier, according to an embodiment. The disposable barrier 285 includes an inlet 289, and the inlet 289 is formed such that the printer arm assembly including upper arm 220 and lower arm 230 may be inserted from a first side 1 into inlet 289. A lower perimeter 10 of disposable barrier 285 extends past a disposable print platform 2, such that disposable print platform 2 is surrounded by barrier 285. The disposable print platform 2 may be provided above the stage 111 discussed above, in some embodiments. The disposable print platform may be replaced when the barrier 285 is replaced, for example, after each printing session when a designated number of 3D structures are fabricated, or at a different time. The disposable print platform 2 may be configured to envelope stage 111 in at least one embodiment. The disposable print platform may be smaller than the stage 111 but large enough such that a plurality of fabricated structures may be created thereon. In at least one embodiment, disposable print platform 2 may be formed as a circular disc or in any shape conforming or non-conforming to a shape of stage 111. Disposable print platform 2 may comprise a plastic sheath over a print bed made of a metal, metal alloy, plastic or any combination thereof. In at least one embodiment, disposable print platform 2 comprises stainless steel and/or plastic. Attachment tabs 11 may be located on the corners to hook to anchor points on the printing assembly, e.g., on housing 101.

Figure 6B:
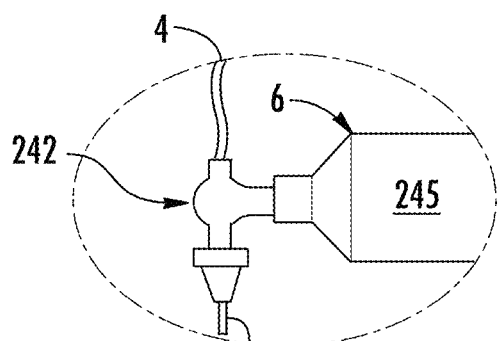
FIG. 6B is a detail view of a portion of the system shown in FIG. 6A.

FIG. 6B is a detail view of a portion of the system shown in FIG. 6A. The system further comprises a passage 4 for connecting a material loading port 3 to valve 242. In at least one embodiment, the passage 4 is a hollow tube. The valve 242 is communicated with syringe 245 and the valve 242 rotates to allow extrusion through tip 247. In at least one embodiment, tip 247 may have at least one tapered side. Further, in another embodiment, tip 247 may have a straight profile, without tapered sides. A tip configuration may be adjusted to achieve particular fluid behavior of the material being deposited by syringe 245.

Figure 6C:
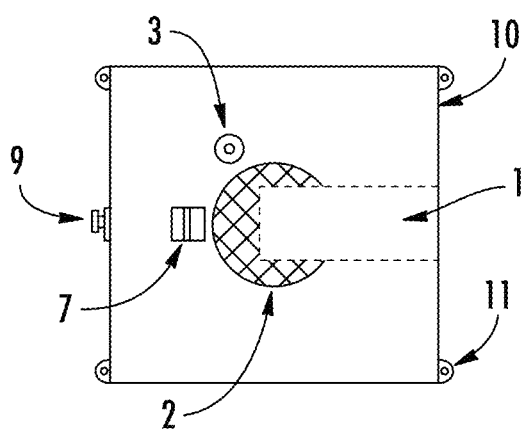
FIG. 6C is a top view of a portion of a system including a disposable barrier, according to an embodiment.

FIG. 6C is a top view of a portion of a system including a disposable barrier, according to an embodiment. A plurality of ports 3, 9 are provided, which may be luer locks, i.e., fluid fittings establishing leak-free communication between the barrier 285 or components therein, and an outside thereof. The ports 3 may be used to load biomaterial into syringe 245, for example. By way of further example, port 9 may be used to pressurize the barrier 285 with sterile air prior to fabrication of 3D structures. In one embodiment, the barrier 285 may be pressurized and held at about 1 to about 75 psi, about 14 to about 75 psi, about 20 to about 75 psi, about 14 to about 65 psi, about 14 to about 50 psi, about 14 to about 40 psi, about 11 to about 20 psi, about 14 to about 17 psi, above about 11 psi, about 12 psi, 15 psi, or about 17 psi and ranges between any two values or less than any one of these values. In particular, the barrier 285 may be pressurized and held at atmospheric pressure, which may be maintained for a duration of the printing (3D structure fabrication). Holding the disposable barrier 285 at such pressure allows for the structure of disposable barrier 285 to be maintained, e.g., in a cuboid shape, and provides sufficient clearance within barrier 285 for fabrication of 3D structures.

Figure 6D:
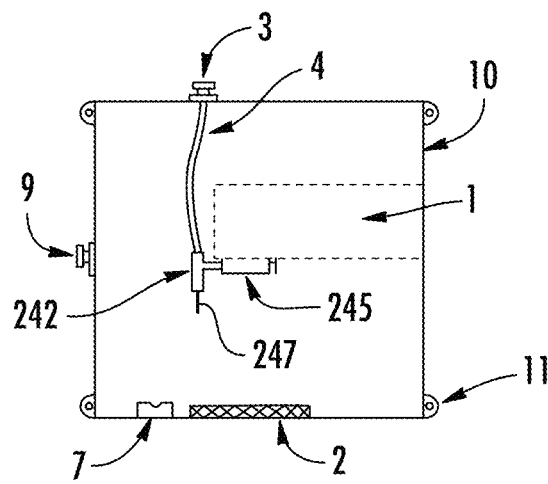
FIG. 6D is a side view of a portion of a system including a disposable barrier, according to an embodiment.

FIG. 6D is a side view of a portion of a system including a disposable barrier, according to an embodiment. As shown in FIG. 6B, a cleaning mechanism 7 may be provided at a base of barrier 285 proximate to syringe tip 247. The cleaning mechanism 7 may be a wiper or squeegee. The syringe tip 247 may be controlled so as to contact cleaning mechanism 7 to thereby clean tip 247. For example, by causing tip 247 to contact cleaning mechanism 7, remaining material on tip 247 may be cleansed from tip 247. The cleaning mechanism 7 may be formed of spongiform material which is replaced at regular intervals, e.g., when barrier 285 is disposed of.

Operation

Figure 7:
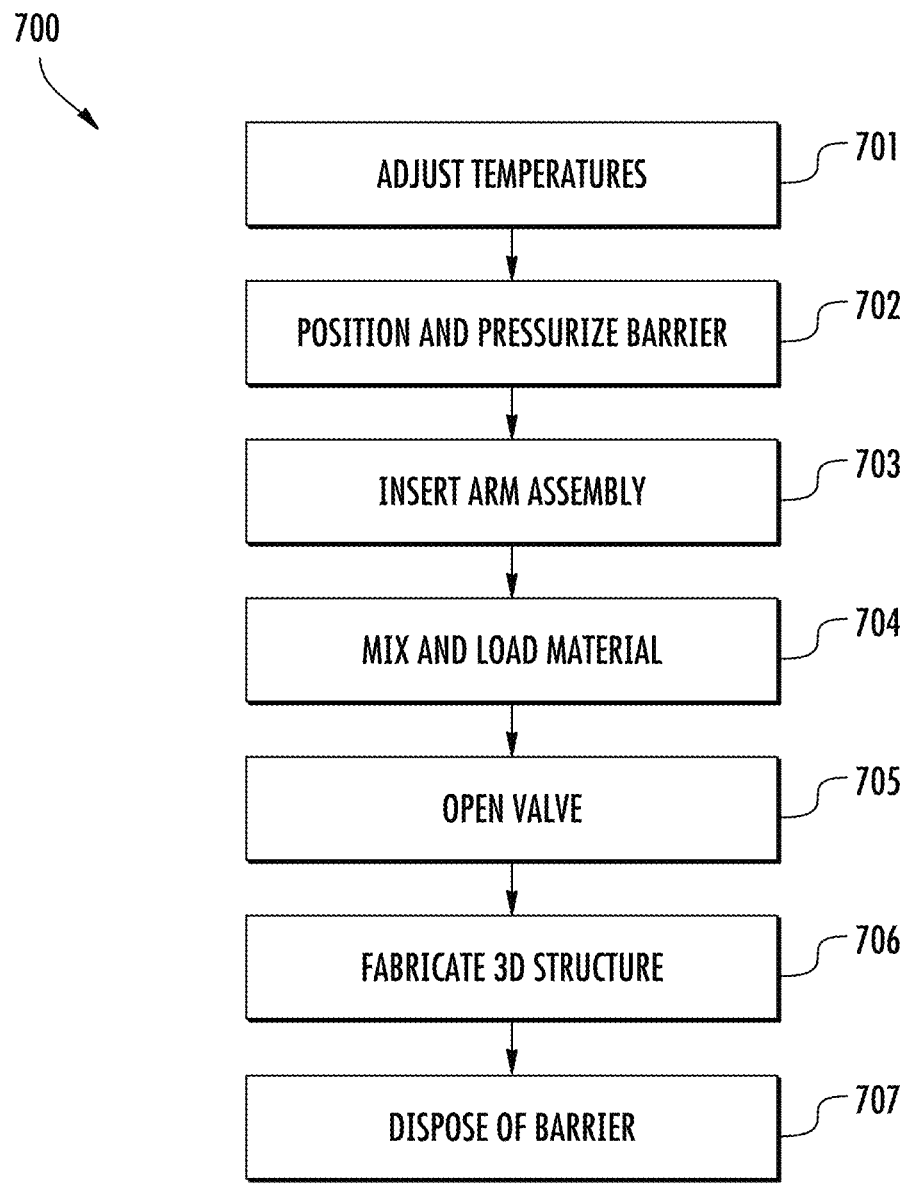
FIG. 7 is a flowchart describing a method of printing, according to an embodiment.

FIG. 7 is a flowchart showing a method of printing, according to at least one embodiment. Specifically, FIG. 7 shows a process 700 for fabricating a 3D structure using the system(s) of one or more embodiments described above. The order of operations enumerated herein is exemplary, and the present disclosure is not limited to the exemplary order shown in FIG. 7. In at least one embodiment, the process 700 includes adjusting temperatures of one or more components of the printer system, at step 101. For example, as mentioned above, the arms 220, 230 may be cooled and the print bed may be heated. The process 700 further includes positioning and pressurizing barrier such as barrier 285 at step 702. For example, positioning the barrier 285 may include locating the barrier 285 so as to cover chassis 120, and providing attachment tabs or clips 11 to secure barrier 285 in place. The locations of the attachment tabs or clips 11 are attachment points at which barrier 285 connects to the printer assembly. In at least one exemplary embodiment, the attachment tabs or clips 11 may include, but are not limited to, hooks, snaps, magnets, vacuum devices, suction cups, screws, and clamps, for example.

Referring again to step 702 of process 700, the barrier 285 may be pressurized as described above, for example, by introducing sterile air via one or more ports. Further, the arm assembly, including upper arm 220, lower arm 230, and connections therebetween, and the syringe 245 may be positioned in inlet 289, at step 703. Tip 247 is not encased within inlet 289, but exposed to the environment within barrier 285. Further, material such as biomaterial is mixed and loaded into a passage 4 via a port 3 so as to be transferred to syringe 245, at step 704. The valve 242 may be opened to permit passage of biomaterial to reach the deposition tip 247, at step 705. The tip 247 may deposit material on a print bed, such as disposable print platform 2 or directly on stage 111. The material is deposited on the print bed in successive layers, thereby forming one or more 3D structures, at step 706. For example, the arm assembly may be manipulated to carry out deposition of an initial layer of biomaterial at one or more locations on the print bed, followed by subsequent layers of biomaterial. In at least one embodiment, the barrier does not move while the arms move within the barrier. Following fabrication, the barrier may be disposed of, at step 707. Further, the printer system or individual components thereof may be washed down after fabrication.

In at least one embodiment, a method of assembling an aseptic printer includes cleaning a receptacle, such as a syringe 245, and attaching the receptacle to a valve 242, e.g., a stopcock. The valve 242 may be attached to the syringe 245 at one end of the syringe 245, for example, at a first side of a first end of the syringe 245. The valve 242 controls a direction of flow to permit ingress of material into the receptacle. Next, the deposition tip 247 is attached to the receptacle. For example, the deposition tip 247 may be attached to the syringe 245 at a second side of the first end of the syringe 245, such that the valve 242 and deposition tip 247 are provided on opposed sides at one end of the syringe 245. In this manner, the deposition tip 247, the syringe 245 and valve 242 may be assembled together.

Following assembly of the deposition tip 247, the syringe 245 and valve 242 together, the assembled components (deposition tip 247, syringe 245, and valve 242) may be connected to a holder. The holder secures the assembled components. In some embodiments, the assembled components may be clipped into the holder at one or more points along the holder. Once the assembled components are secured in the holder, the holder, together with print platform 2, is disposed in the disposable barrier 285. The disposable barrier may be, in some exemplary embodiments, a bag outfitted with at least one aperture that is configured to be closed by a lid. For example, the lid may be removed or secured onto the bag by screwing the lid off or on to the bag. The aperture of such embodiments is dimensioned to receive at least the holder into which the tip 247, syringe 245, and valve 242 are secured, as well as the print platform 2. Once the holder and print platform 2 are inserted into the barrier 285, the lid of the barrier 285 may be positioned to close the barrier 285, thus sealing the interior of barrier 285.

According to at least one embodiment, following closure of the lid on the barrier 285, the barrier 285 is sterilized using an exemplary sterilization process as described above. The barrier 285 is aligned and positioned on the printer chassis 120. Further, the print platform 2 is aligned and positioned in a desired location on the chassis 120, within the barrier 285, and without opening or penetrating the barrier 285. The barrier 285 is then inflated with sterile air to achieve a constant volumetric capacity within the barrier 285 following inflation. A plunger 240 is loaded with biomaterial through at least one port provided on a side of the barrier 285. The port is connected through a hose to the valve 242 within the barrier 285. A position of the valve 242 may be adjusted within the barrier, e.g., by manipulating the valve 242 manually, for example, where such manipulation may be performed by manual movement occurring outside the barrier 285. Thus, in at least one embodiment, the valve 242 is opened or closed without penetrating the barrier 285, such that the barrier 285 remains intact. Once the valve 242 is opened, material is permitted to flow to reach the deposition tip 247.

In at least one embodiment, to fabricate the one or more 3D structures, the printer assembly may be controlled by being electrically or communicatively coupled to a controller. The controller is configured to control the printer assembly, for example, to deposit material on platform 2 or stage 111 in accordance with a control program. The control program may plan a path for the syringe 245 to travel, for example, and may control deposition based on factors such as rheological and fluid dynamic properties (e.g., non-Newtonian behavior) of the biomaterial and the shape of the 3D structure to be fabricated.

The controller may also be configured to control one or more of the motors 120, 255, 280 and 299, and/or valve 242. The controller may include a microprocessor, an application-specific integrated circuit (ASIC), a field-programmable gate array (FPGA), etc., or combinations thereof. The controller may include non-volatile memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller can read instructions. The instructions may include code from any suitable programming language. The controller may also control the printer assembly based on information stored in the memory, such as measurement data relating to a tilt of stage 111, so as to compensate for tilting.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various example implementations are illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. When the language "a portion" is used the item can include a portion and/or the entire item unless specifically stated to the contrary.

The invention claimed is:

1. A printer system, comprising:
   an arm assembly connected to a printer housing;
   a print surface above which a deposition tip connected to the arm assembly is configured to deposit material; and
   a disposable barrier having an inlet formed in the disposable barrier surrounding the print surface, the inlet being structured to isolate the print surface from the arm assembly which is disposed in the inlet,
   wherein motion of the arm assembly is permitted within the inlet, and the deposition tip is not encased within the inlet and is exposed to an environment within the disposable barrier.

2. The printer system of claim 1, further comprising:
   a valve configured to communicate with the deposition tip,
   wherein the valve is configured to permit movement of biomaterial through a passage to the deposition tip.

3. The printer system of claim 2, further comprising:
   a syringe, the valve being attached to the syringe at a first side of the syringe,
   wherein the valve is disposed between the deposition tip and the syringe.

4. The printer system of claim 2, wherein:
   a position of the valve is adjustable without penetration of the barrier.

5. The printer system of claim 1, wherein the barrier comprises a disposable sleeve configured to connect to the printer housing at a plurality of attachment points.

6. The printer system of claim 1, wherein:
   the barrier comprises a plurality of ports;
   at least one of the plurality of ports permits ingress of biomaterial to a passage communicated with the deposition tip such that the biomaterial flows to the deposition tip; and
   at least one of the plurality of ports permits introduction of sterile air within the barrier.

7. The printer system of claim 1, further comprising:
   wherein the inlet is structured to receive at least the deposition tip, and
   wherein the print surface is disposed atop a disposable print bed.

8. The printer system of claim 1, wherein the print surface is formed on a stage, and the stage comprises:
   a skirt portion; and
   a motor configured to adjust a height of the stage.

9. A printer system, comprising:
   an arm assembly including a first arm configured to be driven by a first motor, a second arm configured to be driven by a second motor, and an extruding system including a deposition tip configured to deposit material on a print surface;
   a lead screw which at least one of the first motor or the second motor is configured to rotate via a coupler; and
   a lead screw nut configured to travel along the lead screw so as to rotate a linkage communicated with the first arm,
   wherein at least the first motor, the second motor, the lead screw and the lead screw nut are encased so as to be isolated from an outside environment, and
   wherein the first arm is an upper arm configured to rotate around a first shaft the second arm is a lower arm configured to rotate around a second shaft and the linkage connects the lower arm to the upper arm.

10. The printer system of claim 9, wherein the extruding system further comprises:
    a syringe configured to deliver biomaterial to the deposition tip;
    a plunger configured to engage with an actuator; wherein the lead screw is configured to be rotated by at least one pulley so as to move the actuator into and out of the lower arm.

11. The printer system of claim 9, further comprising:
    a barrier separating the deposition tip from the arm assembly, lead screw and lead screw nut.

12. The printer system of claim 9, wherein:
    the print surface is provided on an elevated stage, a height of the elevated stage being adjustable;
    the elevated stage is mounted to a chassis, and a skirt portion between the print surface and the chassis is configured to expand or contract, and to separate the print surface from the chassis, and the chassis is encased by a housing.

13. The printer system of claim 12, wherein at least one pulley is disposed beneath the print surface, and the pulley is configured to rotate a screw to thread into a drive block which is attached to the elevated stage.

14. The printer system of claim 9, further comprising:
    a contact assembly comprising:
      a pad disposed on an elastic member, and
      at least two contacts,
    wherein, in response to detection of pressure on the pad, a circuit is established between the at least two contacts;
    a plurality of guide pins configured to support the stage; and
    a plurality of bushings encasing respective guide pins of the plurality of guide pins.

* * * * *